United States Patent [19]

Snyder

[11] Patent Number: 5,595,979
[45] Date of Patent: Jan. 21, 1997

[54] METHOD OF TREATING A NEOPLASTIC DISEASE STATE BY CONJUNCTIVE THERAPY WITH 2'-FLUOROMETHYLIDENE DERIVATIVES AND RADIATION OR CHEMOTHERAPY

[75] Inventor: Ronald D. Snyder, Loveland, Ohio

[73] Assignee: Merrell Pharmaceuticals Inc., Cincinnati, Ohio

[21] Appl. No.: 495,720

[22] Filed: Jun. 27, 1995

Related U.S. Application Data

[63] Continuation of Ser. No. 273,242, Jul. 11, 1994, abandoned.

[51] Int. Cl.$^6$ .................................................. A61K 31/505
[52] U.S. Cl. .................................................. 514/49; 514/274
[58] Field of Search ........................................ 514/49, 274

[56] References Cited

U.S. PATENT DOCUMENTS

| | | | |
|---|---|---|---|
| 3,472,837 | 10/1969 | Verheyden et al. | 260/211.5 |
| 4,199,574 | 4/1980 | Schaeffer | 424/200 |
| 4,334,063 | 6/1982 | Spry | 544/28 |
| 4,894,364 | 1/1990 | Greer | 514/49 |
| 5,026,835 | 6/1991 | Ueda et al. | 536/23 |
| 5,047,520 | 9/1991 | Matsuda et al. | 536/23 |
| 5,378,693 | 1/1995 | McCarthy et al. | 514/45 |
| 5,401,726 | 3/1995 | Ueda et al. | 514/49 |
| 5,508,393 | 4/1996 | McCarthy et al. | 536/28.5 |

FOREIGN PATENT DOCUMENTS

| | | |
|---|---|---|
| 0143987 | 6/1985 | European Pat. Off. . |
| 0310673 | 3/1988 | European Pat. Off. . |
| 0372268 | 11/1989 | European Pat. Off. . |
| 0345751 | 12/1989 | European Pat. Off. . |
| 0349243 | 1/1990 | European Pat. Off. . |
| 0468866 | 1/1992 | European Pat. Off. . |
| 0477871 | 4/1992 | European Pat. Off. . |
| 1113851 | 5/1968 | United Kingdom . |
| 8302723 | 8/1983 | WIPO . |
| 9320825 | 10/1993 | WIPO . |
| 9323414 | 11/1993 | WIPO . |
| 9412188 | 6/1994 | WIPO . |

OTHER PUBLICATIONS

Matsuda et al, "Alkyl Addition Reaction of Pyrimidine, 2'-Ketonucleosides: Syntheses of 2'-Branched-Chain Sugar Pyrimidine Nucleosides" *Chem. Pharm. Bull.* 36(3) 945–953 (1988).

Hansske et al., "Nucleic Acid Related Compounds. 43. A Convenient Procedure for the Synthesis fo 2' and 3'-Ketonucleosides" *Tetrahedron Letters*, vol. 24, No. 15, pp. 1589–1592, (1983).

Hansske et al., "2'and 3'-Ketonucleosides and their Arabino and Xylo Reduction Products" *Tetrahedron* vol. 40, No. 1, pp. 125–135, (1984).

Takenuki, et al., *Journal of Medicinal Chemistry* 31:1063–1064 (1988).

Ueda et al, "Synthesis of 2'–Deoxy–8,2'–ethanoadenosine and 3'–Deoxy–8,3'–ethanoadenosine (Nucleosides and Nucleotides. LXIV)" *Chem. Pharm. Bull.* 34(1) pp. 15–23, (1986).

McCarthy et al, *J. Am. Chem. Soc.* 1991, pp. 7439–7440.

Carter et al., *Chemotherapy of Cancer*, second edition, pp. 76–83 (1989).

Sunkara et al, *Proceedings 83 Annual Meeting of the American Association for Cancer Research*, vol. 33, No. 3088, Mar. 1992, p. 517.

Kobayasky et al., *Pharmaceutical Research*, vol. 4, Jul. 4, 1984, pp. 181–183.

Sunkara et al, "Cytotoxicity of Methylglyoxal Bis(guanylhydrazone) in Combination with α–Diflurormethylornithine Against HeLa Cells and Mouse L1210 Leukemia", *JNCI*, vol. 70, No. 3, pp. 505–509 Mar. 1983.

Katritzky, et al, *Comprehensive Heterocyclic Chemistry*, vol. 5, pp. 603 & 989 (1986).

Ueda et al, "Synthesis of 2'(R)–Substituted Neplanocin A's (Nucleosides and Nucleotides XXXVII)", *Chem. Pharm. Bull.* 29(2) pp. 597–600 (1981).

Ferrier, Adv. Carbohydrate Chem. 24:250–251 (1969).

De Clercq, "S–Adenosylhomocysteine Hydrolase Inhibitors as Broad Spectrum Antiviral Agents" *Biochemical Pharmacology*, vol. 36, No. 1, pp. 2567–2575 (11987).

McCarthy et al., J. Am. Chem. Soc. 1991, 113, 7439–7440.

Bitonti A J. et al. Breast Cancer Research and Treatment, vol. 27, No. 1/2. 1993 Bitonti et al.

Rockwell et al, Oncology Research vol. 4, No. 4/5 1992, pp. 151–155.

Snyder, Oncology Research, vol. 6, Nos. 4/5, pp. 177–182, 1994.

Patel, et al, The Cancer Journal, vol. 5, N. 5 Sep. Oct. 1992.

*Primary Examiner*—Paul J. Killos
*Assistant Examiner*—Barbara S. Frazier
*Attorney, Agent, or Firm*—William R. Boudreaux

[57] ABSTRACT

The present invention relates to a method of treating a patient afflicted with a neoplastic disease state comprising the administration thereto of an effective antineoplastic amount of ionizing or nonionizing radiation, or an effective antineoplastic amount of a DNA-reactive chemotherapeutic agent in conjunctive therapy with an effective sensitizing amount of a compound of formula (I).

8 Claims, 4 Drawing Sheets

METHOD OF TREATING A NEOPLASTIC DISEASE STATE BY CONJUNCTIVE THERAPY WITH 2'-FLUOROMETHYLIDENE DERIVATIVES AND RADIATION OR CHEMOTHERAPY

This is a continuation of application Ser. No. 08/273,242, filed Jul. 11, 1994, now abandoned, which is herein incorporated by reference.

BACKGROUND OF THE INVENTION

Neoplastic disease states in humans are recognized throughout the world as being serious and oftentimes life-threatening conditions. These neoplastic diseases, which are characterized by rapidly-proliferating cell growth, have been and continue to be the subject of worldwide research efforts directed toward the identification of therapeutic agents which are effective in the treatment of patients suffering therefrom. Effective therapeutic agents can be characterized as those which prolong the survivability of the patient, which inhibit the rapidly-proliferating cell growth associated with the neoplasm, or which effect a regression of the neoplasm. Research in this area is primarily focused toward identifying agents which would be therapeutically effective in humans. Typically, compounds are tested for antineoplastic activity in small mammals, such as mice, in experiments designed to be predictive of antineoplastic activity not only in those animals but also in humans against specific neoplastic disease states.

Radiosensitizing agents, also known as radiosensitizers, are defined as agents which sensitize cells or organisms to the deleterious cellular effects of exposure to ionizing or nonionizing radiation. These deleterious cellular effects include disruption in cellular function, cell death, and the like. These agents, administered prior to or during exposure, would enhance the severity of deleterious cellular effects to neoplasms caused by exposure to ionizing or nonionizing radiation administered during cancer radiation therapy.

Furthermore, certain radiosensitizing agents provide a sensitization for deleterious cellular effects in cancer cells caused by certain DNA-reactive agents such as cisplastin, cyclophosphamide, diethylnitrosoamine, benzo(a)pyrene, carboplatin, doxorubicin, mitomycin-C and the like. Many of these DNA-reactive agents are chemotherapeutic agents useful in cancer therapy. Radiosensitizing agents are useful in enhancing the severity of deleterious cellular effects in cancer cells caused by exposure to these DNA-reactive agents, such as during cancer therapy with DNA-reactive chemotherapeutic agents.

Ribonucleotide reductase inhibitors, as a class, are known to be effective inhibitors of DNA repair in mammalian cells, see Ben-Hur, E., et al., *Photochem. Photobiol.* 13: 337–345 (1971); Francis, A. A., et al., *Biochim. Biophys. Acta* 563: 385–392 (1979); and Snyder, R. D., *Cell Biol. Toxicol.* 1:81–94 (1984). Specifically, certain 2'-halomethylidene derivatives, such as (E)-2'-deoxy-2'-fluoromethylidenecytidine, are well known as effective antineoplastic agents; see European Patent Application Publication No. 0 372 268, published Jun. 13, 1990. These 2'-halomethylidene derivatives, such as (E)-2'-deoxy-2'-fluoromethylidenecytidine are ribonucleotide reductase inhibitors with potent antiproliferative and antitumor activity which are also useful in the treatment of patients suffering from a variety of neoplastic disease states. Furthermore, a recent report demonstrates that the compound 2',2'-difluorodeoxycytidine provides a radiosensitizing effect in a murine mammary tumor cell line; Rockwell, S., Oncology Res. 4:151–155 (1992).

Applicant has discovered that treating a patient afflicted with certain neoplastic disease states prior to or during radiation or chemotherapy therapy with (E)-2'-deoxy-2'-fluoromethylidenecytidine will provide a sensitizing effect. A sensitizing effect is achieved when a greater antineoplastic effect results with a conjunctive therapy than use of either drug or therapy alone. Specifically, (E)-2'-deoxy-2'-fluoromethylidenecytidine provides a selective sensitization for deleterious cellular effects in cancer cells.

SUMMARY OF THE INVENTION

The present invention provides a method of treating a patient afflicted with a neoplastic disease state comprising the administration thereto of an effective antineoplastic amount of ionizing or nonionizing radiation in conjunctive therapy with an effective sensitizing amount of a compound of the formula

wherein

V is oxy or methylene and

A is a radical of the formula

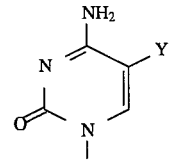

wherein Y is hydrogen, $C_1$–$C_4$ alkyl or $C_1$–$C_4$ alkoxy; or a pharmaceutically acceptable salt thereof.

In addition, the present invention provides a method of treating a patient afflicted with a neoplastic disease state comprising the administration thereto of an effective antineoplastic amount of a DNA-reactive chemotherapeutic agent in conjunctive therapy with an effective sensitizing amount of a compound of formula (I).

The present invention also provides for a method of treating a patient afflicted with a neoplastic disease state comprising the administration thereto of an effective antineoplastic amount of ionizing or nonionizing radiation or an effective antineoplastic amount of a DNA-reactive chemotherapeutic agent in conjunctive therapy with an effective antineoplastic amount of a compound of formula (1), wherein a synergistic effect results.

Furthermore, the present invention provides for a method of treating a patient in need of radiation therapy, or in need of chemotherapy with a DNA-reactive chemotherapeutic agent, comprising administering to said patient a sensitizing amount of a compound of formula (1).

The present invention further provides for a method of sensitizing cancer cells of a patient to the deleterious effects caused by exposure to ionizing or nonionizing radiation, or by exposure to a DNA-reactive agent, comprising contacting said cells with a sensitizing amount of a compound of formula (1).

DETAILED DESCRIPTION OF THE INVENTION

As used herein the term "$C_1$–$C_4$ alkyl" refers to a saturated straight or branched chain hydrocarbon radical of one to four carbon atoms. Included within the scope of this term are methyl, ethyl, n-propyl, isopropyl, n-butyl, isobutyl and the like. The term "$C_1$–$C_4$ alkoxy" refers to an alkyloxy radical made up of an oxygen radical bearing a saturated straight or branched chain hydrocarbyl radical of on to four carbon atoms and specifically includes methoxy, ethoxy, propyloxy, isopropyloxy, n-butyloxy, isobutyloxy, sec-butyloxy, tertiary butyloxy and the like. As used herein the term "$C_2$–$C_7$ alkyl" refers to a saturated straight or branched chain hydrocarbon radical of two to seven carbon atoms. Included within the scope of this term are ethyl, n-propyl, isopropyl, n-butyl, isobutyl, sec-butyl, tert-butyl, pentyl, neopentyl, 2-methylbutyl, 3-methylbutyl, hexyl, heptyl and the like. As used herein the term "$C_5$–$C_7$ cycloalkyl" refers to a saturated cyclic hydrocarbon radical of 5 to 7 carbon atoms. Included within the scope of this term are cyclopentyl, cyclohexyl, cycloheptyl and the like. As used herein the term "1,3-dichloro-1,1,3,3-tetraalkyldisiloxane" refers to compounds wherein the alkyl substituents of the 1,3-(1,1,3,3-tetraalkyldisiloxanylidene) are defined by $R_4$. $R_4$ is a $C_2$–$C_7$ alkyl or $C_5$–$C_7$ cycloalkyl substituent. Examples of suitable $R_4$ substituents are ethyl, n-propyl, isopropyl, n-butyl, isobutyl, sec-butyl, tert-butyl, pentyl, neopentyl, 2-methylbutyl, 3-methylbutyl, hexyl, heptyl, cyclopentyl, cyclohexyl, cycloheptyl and the like. The term "halogen" or "halo" refers to a fluorine, chlorine, bromine, or iodine atom. The term "Ar" or "aryl" refers to an aromatic radical of from about 6 to 12 carbon atoms, such as phenyl, naphthyl or phenyl($C_1$–$C_4$)alkyl groups, wherein said groups are optionally substituted with one, two or three substituents selected from the group consisting of $C_1$–$C_4$ alkyl, halo-substituted $C_1$–$C_4$ alkyl, halogen or $C_1$-$C_4$alkoxy. The term "phenyl($C_1$–$C_4$)alkyl" refers to a phenyl group substituted with a $C_1$–$C_4$ alkyl including phenylmethyl, phenethyl and the like. Specifically included within the scope of the term "Ar" or "aryl" are phenyl, p-toluoyl, p-methoxyphenyl, p-chlorophenyl, naphthyl and the like.

The derivatives of formula (I) can be prepared as described in European Patent Application Publication No. 0 372 268, published Jun. 13, 1990. Additionally, more preferred synthetic processes of the compounds used in the invention are set forth in Schemes A and AI. All of the substituents, unless otherwise indicated, are previously defined. The reagents and starting materials for use in this process are readily available to one of ordinary skill in the art.

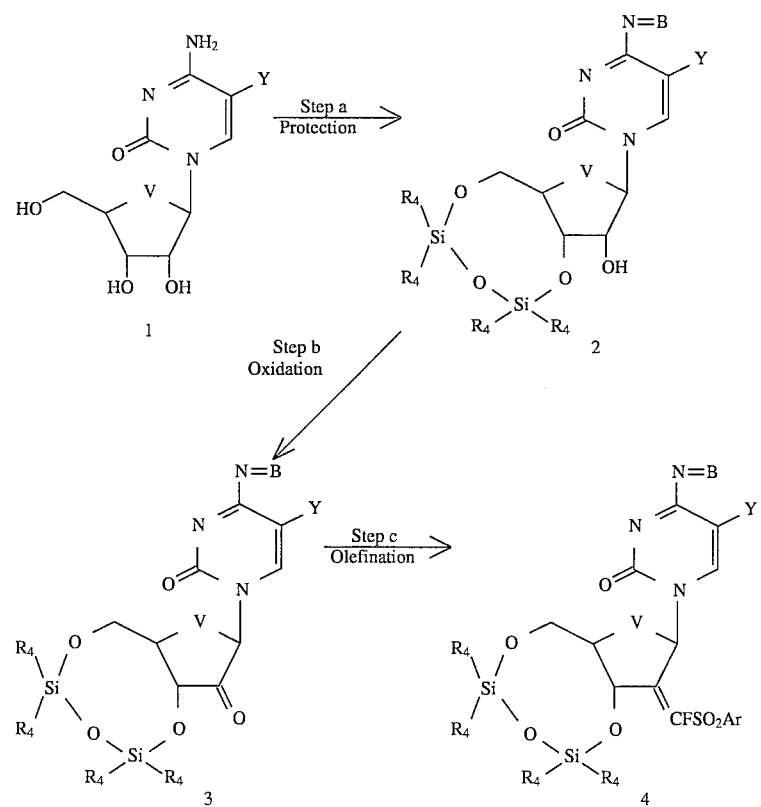

Scheme A

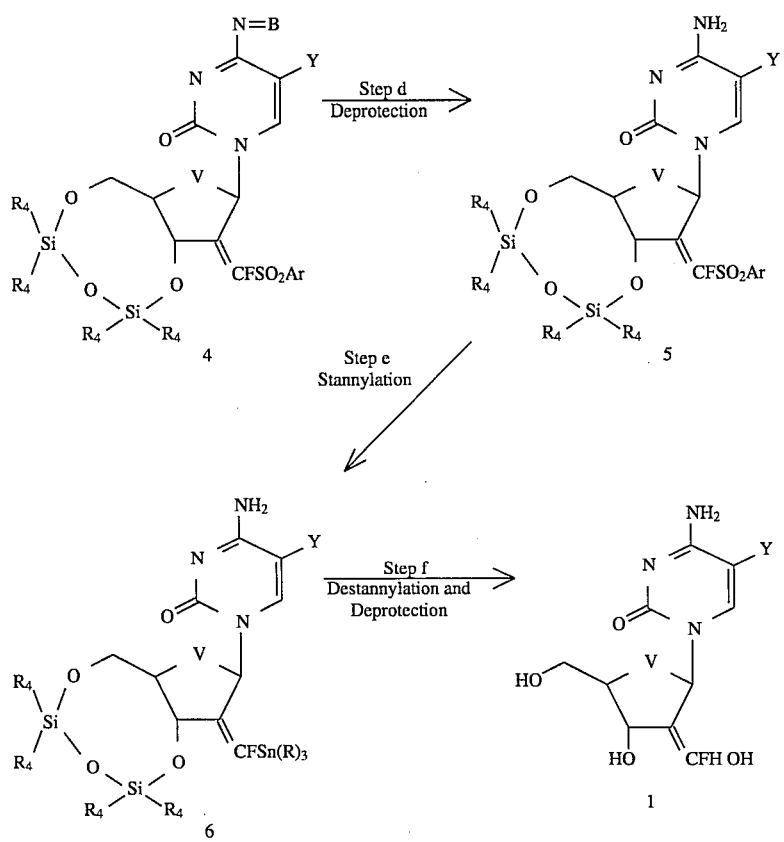

In Scheme A, step a, the 3' and 5' hydroxyls of the appropriately substituted cytidine derivative of structure (1) are protected as the 1,3-(1,1,3,3-tetraalkyldisiloxanylidene) derivative and the amino function is protected with a suitable nitrogen blocking group to provide the compound defined by structure (2). The alkyl substituents of the 1,3-(1,1,3,3-tetraalkyldisiloxanylidene) are defined by $R_4$. $R_4$ is a $C_2$–$C_7$ alkyl or $C_5$–$C_7$ cycloalkyl substituent. Examples of suitable $R_4$ substituents are ethyl, n-propyl, isopropyl, n-butyl, isobutyl, sec-butyl, tert-butyl, pentyl, neopentyl, 2-methylbutyl, 3-methylbutyl, hexyl, heptyl, cyclopentyl, cyclohexyl, cycloheptyl and the like. The preferred $R_4$ substituents are isopropyl, isobutyl, cyclopentyl and the like. The most preferred $R_4$ substituent is isopropyl. A suitable nitrogen blocking group is bound to nitrogen as the imine derivative and is stable to oxidizing conditions such as methyl sulfoxide/oxalyl chloride and to strong organic bases, such as lithium diisopropylamide. For example, suitable nitrogen blocking groups would be N-(N',N'-dimethylaminomethylene)amine, N-(methyl-N',N'-dimethylaminomethylene)amine, N-(methyl-N',N'-diethylaminomethylene)amine, N-(ethyl-N',N'-diethylaminomethylene)amine, and the like. The preferred nitrogen blocking is N-(N',N'-dimethylaminomethylene)amine.

More specifically, in Scheme A, step a, the cytidine derivative (1) is treated with an equivalent of 1,3-dichloro-1,1,3,3-tetraalkyldisiloxane in a basic organic solvent, such as pyridine and allowed to stir for 12 to 24 hours at approximately 10° C. to 30° C. The 1,3-dichloro-1,1,3,3-tetraalkyldisiloxane is readily available to one of ordinary skill in the art, for example see Zhang, H. X., et al., *Synthetic Communications*, 17(11), 1299–1307 (1987). An excess of dimethylformamide dimethyl acetal is then added to the reaction which is allowed to stir for 2 to 6 hours. The solvent is removed under vacuum and the residue is purified by techniques well known to one skilled in the art to provide the compound defined by structure (2).

In Scheme A, step b, the 2'-hydroxyl group is oxidized to the ketone derivative defined by structure (3) by oxidation methods well known to one skilled in the art.

For example, approximately 1.5 equivalents of oxalyl chloride is dissolved in a suitable anhydrous organic solvent, such as methylene chloride, and cooled to about −75° C. To this solution is added 3 equivalents of methyl sulfoxide dropwise, maintaining the temperature below −55° C. An equivalent of the product defined by structure (2) is dissolved in a suitable amount of anhydrous organic solvent, such as methylene chloride, and added slowly to the reaction with stirring. After addition is complete the reaction is stirred for approximately 30 minutes at −75° C., an excess of a suitable organic base, such as triethylamine, is added and the reaction is allowed to warm to room temperature. The ketone derivative (3) is then isolated and purified by techniques well known to one skilled in the art. For example, silica gel chromatography followed by recrystallization from a suitable organic solvent or solvent mixture, such as 10% chloroform/hexane provides the ketone derivative (3).

In Scheme A, step c, the ketone derivative (3) can be olefinated to yield the corresponding exocyclic fluorovinyl sulfone (4) by reaction with a phosphorus ylide which can be prepared according to procedures which are well known and appreciated in the art of chemistry as described by March ["Advanced Organic Chemistry: Reactions, Mechanisms and Structure", McGraw-Hill Book Company, 2nd Ed., 1977, 864–872].

More specifically, olefination may be performed by reacting the appropriately substituted ketone derivative (3) with a suitable phosphonate ylide of formula $(X)_2OP=CF(SO_2Ar)$ through a modification of the Wittig reaction as described by Wadsworth et al. [J. Am. Chem. Soc. 1961, 83, 1733]. For example, the appropriately substituted phosphonate of formula $(X)_2OPCHF(SO_2Ar)$ is dissolved in a suitable anhydrous organic solvent and cooled to approximately −70° C. A suitable anhydrous organic solvent includes hydrocarbon solvents, dialkyl ethers, $C_1$–$C_6$ alkanes, tetrahydrofuran and the like. The preferred anhydrous organic solvent is tetrahydrofuran. An equivalent of a strong base is added slowly to produce the ylide. A wide variety of bases can be used including alkoxides and organometallics, such as alkyllithium, lithium dialkylamide, sodium hydride and the like. The preferred bases are potassium tert-butoxide and lithium bis(trimethylsilyl)amide. After approximately one hour an equivalent of the appropriately substituted ketone derivative (3) is added to the phosphonate ylide at approximately −60° C. followed by warming to about 0° C. for about 30 minutes and then warmed to room temperature for approximately 2.5 hours. The exocyclic fluorovinyl sulfone (4), is then isolated and purified by techniques well known to one skilled in the art. For example, the reaction is quenched with saturated ammonium chloride and the aqueous layer is extracted with a suitable organic solvent, such as diethyl ether. The organic phase is dried over a suitable drying agent, such as anhydrous magnesium sulfate, filtered and concentrated under vacuum. The crude material is filtered through silica gel with a suitable organic solvent, such as ethyl acetate to provide the exocyclic fluorovinyl sulfone (4).

In Scheme A, step d, deprotection of the exocyclic fluorovinyl sulfone (4) by removal of the nitrogen blocking group to provide the appropriately substituted deprotected amine derivative (5) is performed by dissolving the protected compound in an organic solvent, such as dioxane followed by treatment with an excess of a suitable base. A suitable base is one that is capable of removing the nitrogen blocking group without removing the silyl protecting group at the 3', 5' positions. Examples of suitable bases are ammonium hydroxide, ammonia, methylamine and the like. The preferred suitable base is ammonium hydroxide. The reaction is stirred for about 8 to 24 hours at room temperature and the deprotected amine (5) is isolated and purified by techniques well known to one skilled in the art. For example, the solvent is removed under vacuum azeotroping off the water with addition of ethanol and the crude material is purified by flash chromatography using a suitable solvent mixture, such as 5% hexane/ethyl acetate to provide the deprotected amine (5).

An alternative procedure for preparation of the deprotected amine (5) is performed by dissolving the appropriately substituted exocyclic fluorovinyl sulfone (4) in an organic solvent, such as ethyl acetate and treating with one equivalent of concentrated ammonium hydroxide for approximately 2 hours at room temperature. The deprotected amine (5) is isolated and purified by techniques well known to one skilled in the art. For example, the solvent is removed under vacuum azeotroping off the water with addition of ethanol and the crude material is purified by flash chromatography using a suitable solvent mixture, such as 5% hexane/ethyl acetate to provide the deprotected amine (5).

In Scheme A, step e, stannylation of the deprotected amine (5) utilizing procedures which are known to one of ordinary skill in the art as described by McCarthy et al. [J. Am. Chem. Soc., 1991, 113, 7439] provides the exocyclic (fluorovinyl)stannane of structure (6). For example, the deprotected amine (5) is dissolved in a suitable organic solvent, such as benzene or cyclohexane and treated with an excess of a suitable stannylating reagent of formula $(R)_3SnH$. Suitable stannylating reagents are tributyltin hydride, triethyltin hydride, trimethyltin hydride, triphenyltin hydride and the like. The preferred stannylating reagent is tributyltin hydride. The reaction is then initiated by employing a suitable initiator. Suitable initiators are azobisisobutyronitrile (AIBN), UV light, heat and the like. The preferred suitable initiator is azobisisobutyronitrile (AIBN). A catalytic amount of AIBN is added and the reaction is heated at about 60° to 80° C. for about 18 to 20 hours. Additional AIBN may be added as required to convert all the starting material to product. The additional AIBN can be added portionwise directly or as a solution in tetrahydrofuran during the course of the reaction. The additional amount of AIBN required can be readily determined by one of ordinary skill in the art by following the disappearance of starting material in the reaction utilizing techniques well known in the art, such as HPLC or thin layer chromatography. The product is then isolated and purified by techniques well known to one skilled in the art to provide the exocyclic (fluorovinyl)stannane defined by structure (6). For example, the reaction is concentrated under vacuum and the residue is purified by flash chromatography using a suitable solvent mixture, such as 4% to 6% methanol/methylene chloride to provide exocyclic (fluorovinyl)stannane (6).

In Scheme A, step f, the exocyclic (fluorovinyl)stannane (6) can be sequentially converted to the exocyclic fluorovinyl derivative of Formula I by first destannylating with a protolysis agent under mild conditions in the absence of a fluoride ion source. A suitable protolysis agent will substitute a proton for the stannane substituent. Examples of a protolysis agent are ammonia/methanol, silica gel and the like. The protected exocyclic vinylfluoride is then deprotected by treatment with a suitable acid, such as aqueous hydrochloric acid or a fluoride ion source to provide the exocyclic vinylfluoride of Formula I. Examples of a fluoride ion source are sodium fluoride, potassium fluoride, cesium fluoride, tetrabutylammonium fluoride, ammonium fluoride and the like. The preferred fluoride ion source is potassium fluoride.

For example, in Scheme A, step f, the exocyclic (fluorovinyl)stannane (6) is combined with excess silica gel as described by Stork et al. [J. Am. Chem. Soc. 1987, 109, 2829] in a suitable organic solvent, such as methanol and allowed to stir until removal of the tributyltin is complete. The protected exocyclic vinylfluoride is then isolated and purified by techniques well known to one skilled in the art, such as flash chromatography. This product is then treated with an excess of a fluoride ion source, such as tetrabutylammonium fluoride, in a suitable organic solvent, such as methanol and allowed to stir until the deprotection is complete. The product is then isolated and purified by techniques well known to one of ordinary skill in the art to provide the exocyclic fluorovinyl compound defined by Formula I. For example, the reaction is concentrated under vacuum and purified by flash chromatography using a suitable solvent mixture, such as 50% ethyl acetate/hexane followed by 10% to 20% methanol/ethyl acetate. Recrystallization from methanol/ethyl acetate provides the compound of Formula I.

In Scheme A, step f, the exocyclic (fluorovinyl)stannane (6) can also be destannylated and deprotected concomitantly by reacting it with a protolysis agent and fluoride ion source or a suitable acid to provide the exocyclic vinylfluoride of Formula I.

For example, in Scheme A, step f, the exocyclic (fluorovinyl)stannane (6) is dissolved in a suitable organic solvent, such as methanol, treated with a protolysis agent such as potassium fluoride(KF may be in the dihydrate form), which also acts as a fluoride ion source and the reaction is heated at about 45° to 65° C. for approximately 24 to 48 hours. After cooling, the solvent is partially concentrated and excess silica gel is added. The remaining solvent is removed and the product is isolated and purified by techniques well known to one of ordinary skill in the art to provide the compound defined by Formula I. For example, the reaction is concentrated under vacuum and purified by flash chromatography using a suitable solvent mixture, such as 50% ethyl acetate/hexane followed by 10% to 20% methanol/ethyl acetate. Recrystallization from methanol/ethyl acetate provides the compound of Formula I.

Of course one skilled in the art would understand that the stepwise synthesis as presented in Scheme A is not limited to the particular sequence of steps as presented.

For example, in Scheme A, step c the olefination reaction may be performed subsequent to the deprotection reaction performed in step d.

An additional general synthetic process for preparation of compounds of formula (I) is set forth in Scheme AI. All the substituents, unless otherwise indicated, are previously defined. The reagents and starting materials for use in this process are readily available to one of ordinary skill in the art.

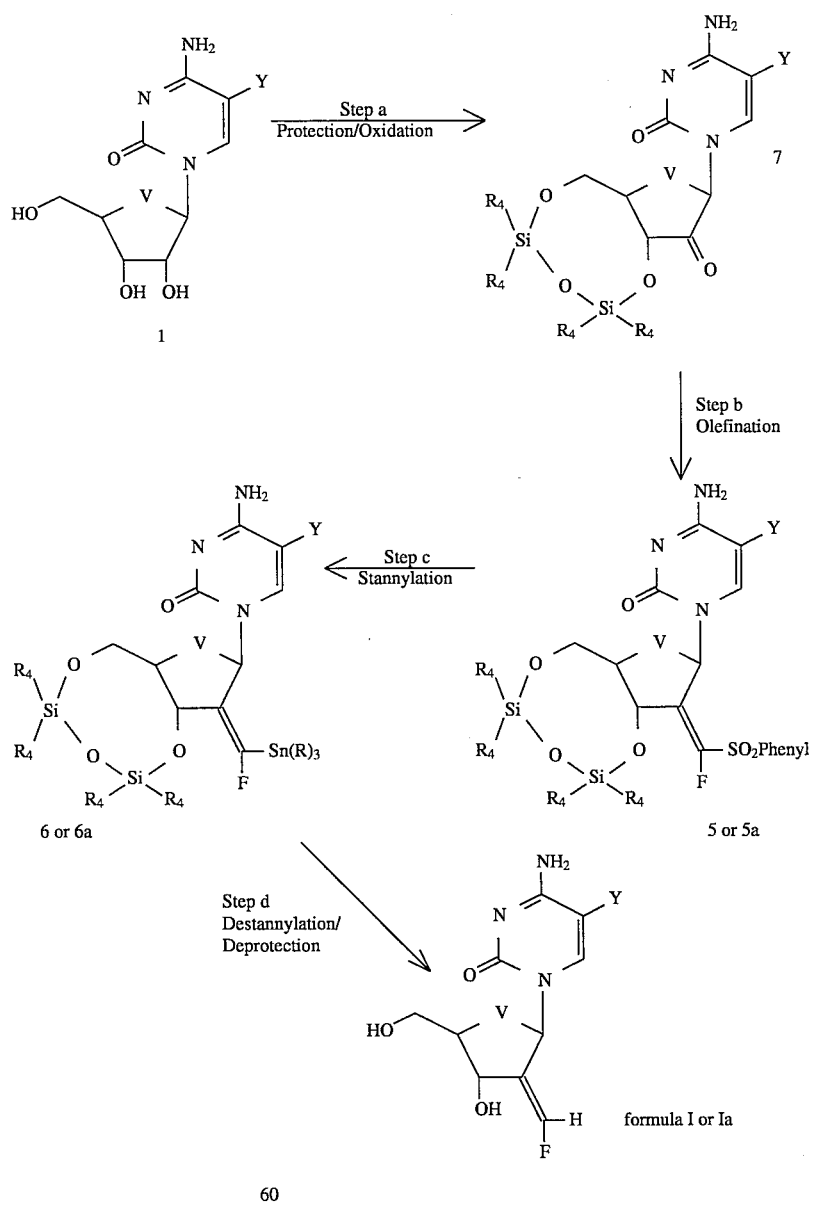

Scheme AI

In Scheme AI step a, the 3' and 5' hydroxyls of the cytidine derivative of structure (1) are protected as the 1,3-(1,1,3,3-tetraalkyldisiloxanylidene) derivative and the 2' hydroxyl is oxidized to the ketone derivative as described by structure (7). For example, cytidine is combined with an excess of 1,3-dichloro-1,1,3,3-tetraalkyldisiloxane in a suitable dry organic solvent, such as pyridine under an inert atmosphere, such as nitrogen. The slurry is stirred at room temperature for about 5 to 24 hours and then cooled to about −17° to 5° C. Approximately 7 equivalents of dry triethylamine are added over a time period of about 1 hour followed by approximately 10 to 11 equivalents of dry dimethyl sulfoxide. Approximately 3 equivalents of $SO_3$-pyridine complex are added and the mixture is stirred at about −5° to 5° C. for about 10 to 20 hours. The reaction is then poured into a mixture of ethyl acetate/water (2:1 by weight) which has been cooled to about 5° C. The original reactor is rinsed with a mixture of ethyl acetate/water (1.2:1.0 by weight) which is added to the previously quenched reaction mixture. Approximately 0.8 equivalents of "OXONE" (potassium peroxymonosulfate) are added to the mixture to oxidize dimethyl sulfide side-product, while maintaining the internal temperature of the reaction mixture below 15° C. The reaction is stirred for about 0.2 hours and then it is filtered to remove salts. The filter cake is rinsed with a suitable organic solvent, such as ethyl acetate. The product is then isolated by techniques well known in the art. For example, the filtrate phases are then separated and the organic phase is rinsed with water. The organic phase is substantially concentrated under vacuum and toluene is added. Again the mixture is substantially concentrated under vacuum. The toluene addition concentration procedure is continued until the distillate is water free. Toluene is again added, the mixture is cooled to about 15° C. and then it is filtered. The filter cake is rinsed with toluene and dried at about 35° C. under a flow of nitrogen to provide the 3',5'-protected-2'-keto derivative (7) as a white solid.

In Scheme AI step b, the 3',5'-protected-2'-keto derivative (7) is subjected to an olefination reaction to provide the (Z)-exocyclic fluorovinyl sulfone described by structure (5) following the procedure described previously in Scheme A step c. More specifically, the olefination reaction can be performed to stereoselectively produce the (Z)-isomer of the exocyclic fluorovinyl sulfone (5a). For example, approximately 1.05 equivalents of diethyl-1-fluoro-1-phenylsulfonylmethanephosphonate and a dry organic solvent, such as tetrahydrofuran are combined under an inert atmosphere such as nitrogen. The mixture is cooled to about −40° C. and an equivalent of ketone derivative (7) is added to the slurry with stirring. The mixture is then cooled to about −50° C. and approximately 1.03 equivalents of a potassium t-butoxide solution (about 20% in tetrahydrofuran) is added dropwise over a period of about 3 hours. After the addition is complete the reaction is allowed to warm to approximately −15° C. over about 3 hours. Additional tetrahydrofuran may be added to aid in stirring as the reaction may thicken. The product is then isolated by techniques well known in the art. For example, the reaction can be quenched by vacuum transferring to an aqueous ammonium chloride solution at room temperature. The mixture is allowed to stir for about 30 minutes. The phases are then allowed to separate. The organic phase containing the (Z)-exocyclic fluorovinyl sulfone (5a) is separated from the aqueous phase and is carried on to step c in Scheme AI.

In Scheme AI step c, the exocyclic fluorovinyl sulfone (5) or the (Z)-exocyclic fluorovinyl sulfone (5a) is subjected to a stannylation reaction to provide the exocyclic (fluorovinyl)stannane or the (Z)-exocyclic (fluorovinyl)stannane described by structures (6) and (6a) under conditions generally described previously in Scheme A step e.

In Scheme AI step d, the exocyclic (fluorovinyl)stannane (6) or the (Z)-exocyclic (fluorovinyl)stannane (6a) can be sequentially or concomitantly destannylated and deprotected to provide the the exocyclic vinylfluoride of Formula I or the (E)-exocyclic vinylfluoride of Formula Ia under conditions generally described previously in Scheme A step f.

The appropriately substituted phosphonate of formula $(X)_2OPCHF(SO_2Ar)$ required for preparation of the phosphonate ylide for reaction in Scheme A in step c and Scheme AI in step b can be obtained by a variety of methods described by Schemes B, C and D.

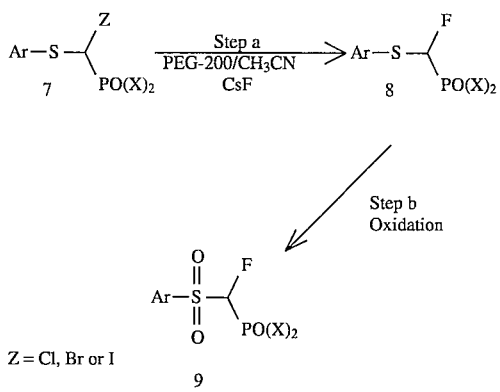

Scheme B

Z = Cl, Br or I

For example in Scheme B, step a, the compound defined by structure (7) is dissolved in a mixture of poly(ethylene glycol):acetonitrile in a ratio of approximately 1:2. A suitable molecular weight range for the poly(ethylene glycol) is between 100 and 400 g/mol. An excess of a fluoride ion source, such as cesium fluoride is added and the reaction is heated to approximately 80° C. for 1 to 24 hours. The reaction is then diluted with water and the product extracted with a suitable organic solvent such as chloroform to provide after drying and concentrating under vacuum the product defined by structure (8). This is then oxidized by techniques well known to one skilled in the art. For example, treatment of compound (8) with potassium peroxymonosulfate in a suitable organic solvent, such as aqueous methanol to provides the appropriately substituted phosphonate defined by structure (9).

The appropriately substituted phosphonate defined by structure (9) can be obtained by another method as described in Scheme C.

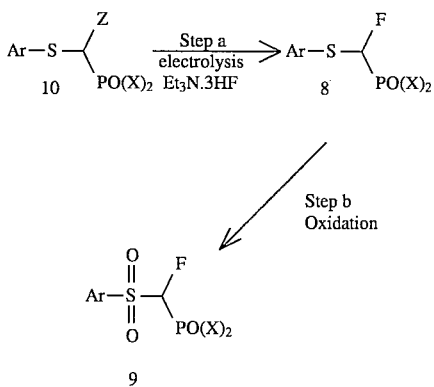

Scheme C

In Scheme C, step a, the compound defined by structure (10) is dissolved in a suitable organic solvent, such as tetrahydrofuran, treated with excess triethylamine trihydrofluoride and the solution is cooled to approximately −78° C.

The solution is then subjected to a controlled potential electrolysis for about 3 to 10 hours to effectuate anodic monofluorination following generally the procedure of Matsue et al. [*J. Chem Soc., Chem. Commun.* 1991, 1028]. The product defined by structure (8) is then isolated and oxidized in step b as described in Scheme B to provide the appropriately substituted phosphonate defined by structure (9).

Additionally, the appropriately substituted phosphonate defined by structure (9) may be prepared in situ as the ylide defined by the formula $(X)_2OP=CF(SO_2Ar)$ as shown in Scheme D.

Scheme D

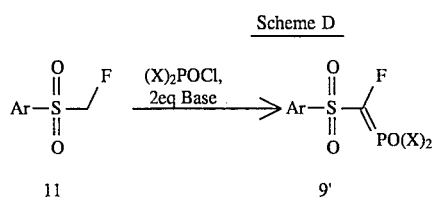

In Scheme D, the appropriately substituted sulfone, such as fluoromethylphenyl sulfone, which can be prepared according to McCarthy et al. [*Tetrahedron Lett.* 1990, 31, 5449], is dissolved in a suitable anhydrous organic solvent, such as tetrahydrofuran, cooled to approximately −70° C. and treated with an equivalent of a dialkyl chlorophosphate, such as diethyl chlorophosphate, defined by the formula $(X)_2POCl$. The solution is then treated slowly with 2 equivalents of a strong base, such as lithium bis(trimethylsilyl)amide. After addition is complete the reaction is stirred at approximately −65° C. for about 1 hour to provide the ylide defined by structure (9').

The following examples present typical syntheses as described by Schemes A, B, C and D. These examples are understood to be illustrative only and are not intended to limit the scope of the invention in any way. As used in the following examples, the following terms have the meanings indicated: "g" refers to grams, "mmol" refers to millimoles, "mL" refers to milliliters, "°C." refers to degrees Celsius, "TLC" refers to thin layer chromatography, "mg" refers to milligrams, "μL" refers to microliters and "δ" refers to parts per million downfield from tetramethylsilane.

EXAMPLE 1

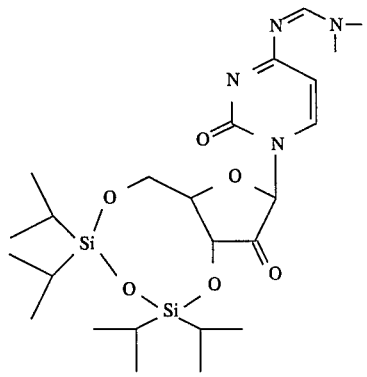

2'-deoxy-N-[(dimethylamino)amino)methylene]-2'-oxo-3', 5'-O-[1,1,3,3-tetrakis(1-methylethyl)-1,3-disiloxanediyl] cytidine.

Scheme A, step a; In a one-neck 2 L round bottom flask equipped with an addition funnel and under a nitrogen atmosphere, treat a slurry of cytidine (100 g, 0.41 mol) in anhydrous pyridine (800 mL) with 1,3-dichloro-1,1,3,3-tetraisopropyldisiloxane (130 g, 0.41 mol). After 30 minutes, everything dissolves. Stir the reaction overnight at room temperature. Add neat dimethylformamide dimethyl acetal (165 g, 1.38 mol) and stir the reaction for 4 hours. The reaction will warm slightly and become cloudy. Remove the pyridine under high vacuum and azeotrope with toluene (2×500 mL) to remove any remaining pyridine. Heat the solid residue with 1 L of ethyl acetate and gravity filter into a 5 L flask. Dissolve the insolubles in water (800 mL) and brine (200 mL) and extract additional product into ethyl acetate (2×600 mL). Dry the solution over anhydrous magnesium sulfate and concentrate under vacuum to provide 90 g of "wet" solid. Dissolve this solid in ethyl acetate (200 mL) and combine with the previous ethyl acetate filtrate. Add hexane (3 L) to the solution, heat and filter while still hot. Allow the solution to sit overnight. Collect the white crystals which form by filtration and dry in a warm vacuum oven to produce compound (142.4 g, 64%). Concentrate the above filtrate and purify the residue by flash chromatography on 1.4 L silica gel (12.5% ethanol/ethyl acetate) to yield an additional amount of compound (17.4 g) from fractions 8–16. Fractions 2–7 contain compound contaminated with pyridine. Concentrate these fractions under vacuum and recrystallize the residue to provide an additional amount of compound (24.5 g) to provide a total amount of 184.2 g (83% yield) of N-[(dimethylamino)methylene]-3',5'-O-[1,1,3,3-tetrakis(1-methylethyl)-1,3-disiloxanediyl]-cytidine as white crystals, mp 137°–138° C.;

$^1$H NMR (CDCl$_3$) δ 0.97–1.10 (m, 28), 3.14 (s, 3), 3.16 (s, 3), 3.98–4.39 (m, 5), 5.82 (s, 1), 6.05 (d, 1, J=7.2 Hz), 7.92 (d, 1, J=7.5 Hz), 8.85 (s, 1); MS (CI/CH$_4$) m/z 541 (MH$^+$).

Anal. Calcd for $C_{24}H_{44}N_4O_6Si_2$: C, 53.30; H, 8.20; N, 10.36. Found: C, 52.93; H, 8.33; N, 10.07.

Scheme A, step b; Flush a 3 neck 2 L flask fitted with a condenser, mechanical stirrer and a thermometer with nitrogen and charge with oxalyl chloride (13.08 mL, 0.15 mol) and anhydrous methylene chloride (750 mL). Cool the solution to −75° C. and add dimethylsulfoxide (21.3 mL, 0.30 mol) dropwise while maintaining the temperature below −55° C. Continue stirring for 5 minutes and then add the protected cytidine formed above in step a (54 g, 0.10 mol) in anhydrous methylene chloride (250 mL) over 10 minutes. Stir for 30 minutes at −75° C. and add triethylamine (75.5 mL, 0.54 mol). Remove the ice bath allowing the reaction to warm to room temperature. After 1 hour at room temperature, dilute the reaction with an equal volume of diethyl ether and stir for an additional hour. Pour the mixture onto silica gel (500 mL) in a fritted funnel and elute with diethyl ether (1 L) followed by methylene chloride (1 L). Concentrate the diethyl ether wash and treat with 10% chloroform/hexane (300 mL). Filter the solid and dry to provide 31.6 g as a white powder. Concentrate the methylene chloride wash and recrystallize the residue from 10% chloroform/hexane (300 mL) to provide an additional 12.5 g for a total of 48.6 g of the title compound (90% yield). This compound readily hydrates at the C-2' position to form the ketone hydrate. It should be protected from prolonged exposure to moisture;

$^1$H NMR (CDCl$_3$) δ 0.99–1.16 (m, 28), 3.13 (s, 3), 3.14 (s, 3), 3.95–4.03 (m, 1), 4.06–4.22 (m, 2), 4.93 (s, 1), 5.22 (d, 1, J=8.0 Hz), 6.02 (d, 1, J=7.2 Hz), 7.29 (d, 1, J=7.2 Hz), 8.82 (s, 1); MS (CI/CH$_4$) m/z 539 (MH$^+$).

Anal. Calcd for $C_{24}H_{42}N_4O_6Si_2$·1/15 CHCl$_3$: C, 52.85; H, 7.75; N, 10.24. Found: C, 52.72; H, 7.86; N, 10.24.

EXAMPLE 2

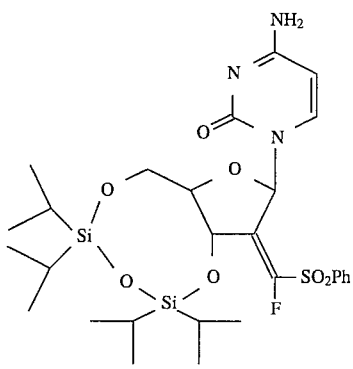

(2'Z)-2'-deoxy-2'-[fluoro(phenylsulfonyl)methylene]-3',5'-O-[1,1,3,3-tetrakis(1-methylethyl)-1,3-disiloxanediyl]cytidine.

Scheme A, steps c and d; Under a nitrogen atmosphere, cool fluoromethylphenyl sulfone (19.4 g, 0.11 mol) in anhydrous tetrahydrofuran (800 mL) to −70° C. and add diethyl chlorophosphate (16 mL, 0.11 mol) via syringe. Next, slowly add 1M lithium bis(trimethylsilyl)amide (200 mL, 0.20 mol) using a dropping funnel. After complete addition maintain the reaction at −65° C. for 1 hour. Add a solution of the above prepared ketone (40 g, 0.074 mol in 200 mL of tetrahydrofuran) using an addition funnel and maintain the temperature at −60° C. After complete addition, warm to 0° C. for 30 minutes and then room temperature for 2.5 hours. Quench the reaction with saturated ammonium chloride (100 mL), dilute with diethyl ether (600 mL) and a small amount of water to dissolve the inorganic salts. Separate the layers and wash the organic phase with saturated sodium chloride. Combine the aqueous washes and back extract with diethyl ether (200 mL). Wash this organic phase with saturated sodium chloride. Combine the organic layers, dry over anhydrous magnesium sulfate, filter and concentrate under vacuum to provide a dark viscous oil (71.8 g). $^{19}$F NMR (CDCl$_3$) shows four peaks, two from protected amino δ −115.21 (Z isomer) and −119.70 (E isomer) and two peaks from the free amino derivative δ −115.62 (Z isomer) and −119.40 (E isomer). The E/Z ratio is 10.4:1. Filter the crude sample through silica gel (1 L) with ethyl acetate (12 L). This step is optional before removing the amino protecting group. Concentrate the filtrate under vacuum to provide a viscous tan oil (46.8 g). Dissolve the oil in dioxane (200 mL) and add concentrated ammonium hydroxide (100 mL). Stir the reaction overnight. Then remove the solvent under vacuum and azeotrope the residue with ethanol (2×300 mL) to remove any residual water. Purify the product by flash chromatography (1.4 L silica gel, 5% hexane/ethyl acetate) to provide the E isomer (20 g). Purify isolated impure material (16 g) from flash chromatography by Prep HPLC (ethyl acetate) to provide additional E isomer (11.4 g) for a total of 31.4 g (66.3% yield) of the title compound. Recrystallize from hexane to provide a white powder, mp waxes at 135° C., clears at 145° C.;

$^1$H NMR (CDCl$_3$) δ 0.97–1.11 (m, 28), 3.93–4.03 (m, 2), 4.09–4.17 (m, 1), 5.68 (d, 1, J=7.2 Hz), 5.72 (br s, 2), 6.43 (t, 1, J=2.0 Hz), 7.33 (d, 1, J=7.5 Hz), 7.46–7.65 (m, 5); $^{19}$F NMR (CDCl$_3$) δ −119.22 (s); MS (CI/CH$_4$) m/z 640 (MH$^+$).

Anal. Calcd for C$_{28}$H$_{42}$FN$_3$O$_7$SSi$_2$: C, 52.56; H, 6.61; N, 6.57. Found: C, 52.40; H, 6.96; N, 6.36.

EXAMPLE 3

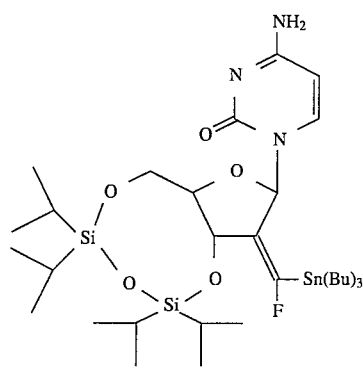

(2'Z)-2'-deoxy-2'-[fluoro(tributylstannyl)methylene]-3',5'-O-[1,1,3,3-tetrakis(1-methylethyl)-1,3-disiloxanediyl]cytidine.

Scheme A, step e; Dissolve the above prepared fluorovinyl sulfone (26 g, 0.0406 mol) in benzene (300 mL) and reflux without a condenser for 15 minutes. Cool the reaction and add tributyltin hydride (32.6 mL, 0.122 mol) and azobisisobutyronitrile (500 mg). Reflux the reaction for 18 hours. Concentrate the reaction under vacuum and purify the residue by flash chromatography (1.4 L silica gel, 4% methanol/methylene chloride, 4 L, followed by 6% methanol/methylene chloride) to provide the title compound (26.5 g, 82.8% yield) as a yellow foam; $^1$H NMR (CDCl$_3$) δ 0.87 (t, 9), 0.94–1.17 (m, 34), 1.22–1.35 (m, 6), 1.38–1.50 (m, 6), 3.78–3.88 (m, 2), 3.96–4.04 (m, 1), 5.18 (br s, 1), 5.82 (d, 1, J=7.5 Hz), 6.76 (br s, 1), 7.21 (d, 1, J=7.7 Hz); $^{19}$F NMR (CDCl$_3$) δ −92.27 (s, 84%) and (d, 16%, J$_{Sn-F}$=219 Hz); MS (CI/CH$_4$) m/z 790 (MH$^+$).

EXAMPLE 4

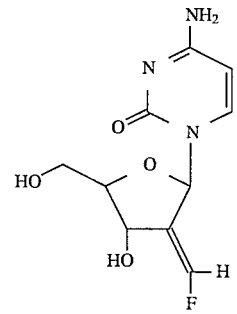

(E)-2'-deoxy-2'(fluoromethylene)cytidine

Scheme A, step f; Dissolve the (fluorovinyl)stannane (26 g, 0.033 mol) and potassium fluoride (9.6 g, 0.165 mol) in methanol (300 mL) and reflux for 24 hours. After cooling, partially concentrate the solution was under vacuum, add silica gel (75 mL) and then concentrate the mixture under vacuum to a free flowing powdery solid. Purify by filtering through silica gel (1 L) with 50% ethyl acetate/hexane (2 L), followed by 10% methanol/ethyl acetate (2 L) and 20% methanol/ethyl acetate (8 L) to provide 9.3 g of compound as a white solid [note- a lower R$_f$ material visible by potassium permanganate stain, elutes with the later fractions. Trituration with diethyl ether lowers the concentration but traces still remain. Partition the product between water and diethyl ether and then lyophilize the aqueous layer to purify]. Recrystallize from methanol/ethyl acetate (120 mL) to yield 4.16 g and a second crop to yield 1.66 g of the title compound (6.26 g total, 68.7%) as white crystals, mp 166° C. (foams); $^1$H NMR (DMSO-$d_6$) δ 3.48–3.62 (m, 2), 3.73–3.78 (m, 1), 4.73–4.78 (m, 1), 4.95 (t, 1, J=5.6 Hz), 5.65 (d, 1, J=6.9 HZ), 5.73 (d, 1, J=7.6 Hz), 6.65–6.68 (m, 1), 6.77 (dt, 1, J=8.13, 2.0 Hz), 7.25 (br s, 1), 7.54 (d, 1, J=7.3 Hz); $^{19}$F NMR (DMSO-$d_6$) δ −130.05 (d, J=80.9 Hz); MS NEG (Cl/CH4) 257 (M$^−$.).

Anal. Calcd for $C_{10}H_{12}FN_3O_4$: C, 46.70; H, 4.70; N, 16.34. Found: C, 46.81; H, 4.71; N, 16.18.

EXAMPLE 5

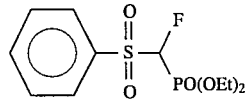

Diethyl 1-fluoro-1-(phenylsulfonyl)methanephosphonate

Scheme B, step a; Charge a 3 neck 100 mL round bottom flask flushed with nitrogen with diethyl 1-chloro-1-(phenylsulfide)methanephosphonate (62 mmol), cesium fluoride (126 mmol) and a mixture of poly(ethylene glycol)-200 and acetonitrile (38 mL of in a 1:2 ratio). Heat the reaction to 80° C. with stirring for 2 hours. Cool the reaction, dilute with water (125 mL) and extract with chloroform (2×125 mL). Combine the organic extracts, wash with water (50 mL), dry over anhydrous magnesium sulfate, filter and concentrate under vacuum to yield diethyl 1-fluoro-1-(phenylsulfide)methanephosphonate.

Scheme B, step b; Dissolve the crude diethyl 1-fluoro-1-(phenylsulfide)methanephosphonate in methanol (85 mL) and cool to 0° C. Add a solution of potassium peroxymonosulfate (63 mmol in 85 mL water) slowly with stirring. The temperature increases to approximately 55° C. After cooling, stir the reaction for 4 hours and then concentrate the reaction under vacuum. Suction filter the remaining slurry through diatomaceous earth and rinse with chloroform. Separate the layers and extract the aqueous with chloroform. Combine the organic extracts, dry over anhydrous magnesium sulfate, filter and concentrate under vacuum. The residue is then purified by techniques well known to one skilled in the art, such as flash chromatography to provide the title compound.

EXAMPLE 6

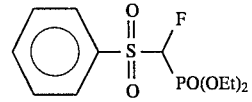

Diethyl 1-fluoro-1-(phenylsulfonyl)methanephosphonate

Scheme C, step a; Cool a solution of diethyl 1-(phenylsulfide)methanephosphonate (20 g, 76.8 mmol) and triethylamine trihydrofluoride (37 g, 230 mmol) in tetrahydrofuran (200 mL) to −78° C. Electrolysis is performed at platinum electrodes (3.8×12 cm) for 15 minutes at 0.5 A and then increased to 1.0 A for 6.25 hours and then stopped. After sitting overnight, continue the electrolysis for an additional 3 hours at 1.0 A for a total time of 9.5 hours. Dilute the reaction with diethyl ether (200 mL) and rinse with 2 molar ammonium hydroxide. Wash the aqueous and extract with diethyl ether (200 mL). Combine the organic phases and dry over anhydrous magnesium sulfate. Filter and concentrate to provide the crude material as a brown oil (27.4 g). Purify the crude material by passing through silica gel (500 g, 60–200 mesh) with ethyl acetate:hexane (1:6, 4 L then 1:3, 2 L) followed by ethyl acetate to provide the diethyl 1-fluoro-1-(phenylsulfide)methanephosphonate (10.7 g, 50%).

Scheme C, step b; Oxidize the diethyl 1-fluoro-1-(phenylsulfide)methanephosphonate (8.4 g, 86% pure) in a manner analogous to that in example 5, step b by dissolving in methanol (200 mL) and treating with potassium peroxymonosulfate (35 g in 300 mL water) to provide the title compound.

EXAMPLE 7

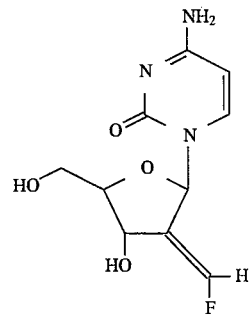

(E)-2'-deoxy-2'(fluoromethylene)cytidine

Scheme A, step f [sequential method]; Dissolve (Z)-2'-deoxy-2'-[fluoro(tributylstannyl)methylene]-3',5'-O-[1,1,3,3-tetrakis(1-methylethyl)-1,3-disiloxanediyl]cytidine (8 g, 0.01 mol) prepared in example 3 in methylene chloride (200 mL), add activated silica gel (approximately 50 g, 60–200 mesh) and stir until TLC indicates the protolysis is complete. Filter the reaction and concentrate the filtrate under vacuum to yield the protected exocyclic vinylfluoride. Dissolve the protected exocyclic vinylfluoride (0.01 mol) in tetrahydrofuran (200 mL) and treat with tetrabutylammonium fluoride (0.025 mol). Stir the reaction until TLC indicates removal of the 3',5' protecting group is complete. The product is then isolated and purified by techniques well known to one of ordinary skill in the art to provide the title compound.

EXAMPLE 8

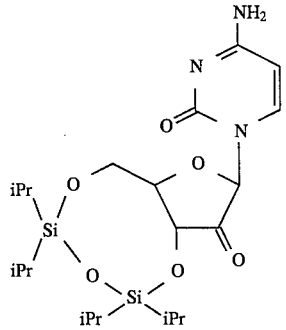

Preparation of 2'-Deoxy-2'-oxo-3',5'-O-[1,1,3,3-tetrakis(1-methylethyl)-1,3-disiloxanediyl]-cytidine.

Cytidine (7 Kg, 28.8 mmol), dry pyridine (29.6 Kg, 374.7 mol) and 1,3-dichloro-1,1,3,3-tetraisopropyldisiloxane (10.0 Kg, 31.7 mol) are loaded into a nitrogen-purged 50 gallon glass lined reactor. The slurry is stirred at room temperature for 6 hours then cooled to −17° C. Dry triethylamine (20.7 Kg, 204.8 mol) is added over one hour. During the addition the reaction temperature rises to −2° C. Dry dimethyl sulfoxide (30.3 Kg, 387.5 mol) and SO$_3$-pyridine complex (14.0 Kg, 87.7 mol) are added in one portion and the mixture is stirred between −5° and 5° C. After 10 hours the mixture is quenched by transferring to a 100 gallon glass-lined reactor containing ethyl acetate (77.3 Kg) and water (32.2 Kg) cooled to 5° C. The original reactor is rinsed with a mixture of ethyl acetate (18.4 Kg) and water (15.1 Kg) and this is transferred to the quench reactor. A 20 wt % solution of OXONE (70.9 Kg, 23.1 mol) is added to the two phase mixture keeping the internal temperature below 15° C. Stir the mixture for 0.2 hours with ethyl acetate (26.4 Kg). Allow the filtrate phases to separate. The bottom aqueous phase is drained and the top organic phase is washed with water (28.4 Kg). The organic phase is then concentrated under vacuum (70 mmHg, 20° C.) to a volume of about 20 gallons. Toluene (173 Kg) is added and the mixture is concentrated under vacuum (60 mm HG, 30° C.) to about 50 gallons. The toluene addition/concentration is continued until the overheads become clear (water free). The mixture is then concentrated under vacuum to about 35 gallons. The mixture is cooled to 15° C. and filtered. The filter cake is rinsed with toluene (177 Kg). The filter cake is then dried at 35° C. under a flow of nitrogen provided the title compound (8.6 Kg, 62%) as a white solid.

EXAMPLE 9

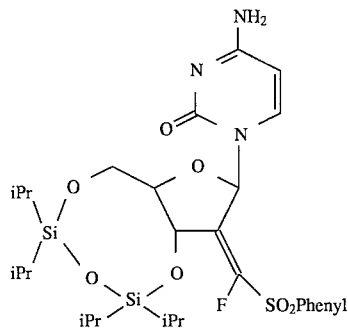

Preparation of (Z)-2'-[fluoro(phenylsulfonyl)methylene]-3',5'-O-[1,1,3,3-tetrakis(1-methylethyl)-1,3-disiloxanediyl]-cytidine.

Diethyl-1-fluoro-1-phenylsulfonylmethanephosphonate (1.391 Kg, 4.483 mol) and dry tetrahydrofuran (8.328 Kg) are combined in a nitrogen-purged five-neck 22 liter round bottom flask equipped with a 6 liter addition funnel, a mechanical stirrer, a nitrogen bubbler and a thermowell. The resulting solution is cooled to −40° C. Ground 2'-deoxy-2'-oxo-3',5'-O-[1,1,3,3-tetrakis(1-methylethyl)-1,3-disiloxanediyl]-cytidine (2.064, 4.266 mol) is then added in one portion and the resulting slurry cooled to −50° C. Potassium t-butoxide (20wt% in tetrahydrofuran, 2.461 Kg, 4.387 mol) is then added dropwise via the addition funnel over 3 hours. After addition is complete, the homogeneous brown mixture is slowly warmed to −15° C. over 3 hours. The mixture thickens during warm-up. Additional tetrahydrofuran (1.294 Kg) is added to improve stirring. The reaction mixture is then quenched by vacuum transferring to a room temperature solution of ammonium chloride (1.706 Kg) in water (5.242 Kg) and this is stirred for 0.5 hours. The phases are then allowed to separate. The bottom aqueous phase is drained and the top organic phase containing the title compound in solution is retained for the next step. HPLC analysis indicates no detectable amount of starting ketone or E-isomer.

EXAMPLE 10

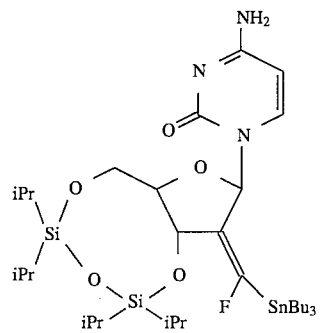

Preparation of (Z)-2'-deoxy-2'-[fluoro(tributylstannyl)methylene]-3',5'-O-[1,1,3,3-tetrakis(1-methylethyl)-1,3-disiloxanediyl]-cytidine.

The above prepared solution of (Z)-2'-[fluoro(phenylsulfonyl)methylene]-3',5'-O-[1,1,3,3-tetrakis(1-methylethyl)-1,3-disiloxanediyl]-cytidine (1.327 Kg) is checked with potassium iodide-starch paper to verify the absence of peroxides and is then concentrated under vacuum (35° C. to 36° C.) to provide a cloudy yellow oil that is 44% to 49% by weight of the above starting material. The material is subjected to azeotropic drying with cyclohexane at 20° C. to 40° C. and 90 to 120 torr. Approximately 9 to 11 kg of cyclohexane is used to effect the drying, affording a final cyclohexane solution that is 46% to 49% by weight of the above starting material. This solution is transferred to a 22 liter round bottomed flask. Additional cyclohexane (0.55 to 1.2 Kg) is used to rinse any cyclohexane residual to the 22 liter round bottom flask. To this solution is added tributyltin hydride (3.6 to 4.0 Kg, 2.5 to 2.7 equivalents) and azoisobutyronitrile (44 to 55 g, AIBN) at room temperature. The stirred reaction mixture is placed under nitrogen and heated to 60° C. to 65° C. The reaction mixture is allowed to stir at this temperature for 18 to 20 hours, during which time a solution of AIBN (240 to 300 g) in tetrahydrofuran (2.5 to 3.4 Kg) is added in a slow stream. The reaction mixture is cooled to room temperature and transferred to a 50 liter bottom drained flask. Tetrahydrofuran (9 to 10 Kg) is added. The resulting solution is extracted with two portions of one normal aqueous potassium hydroxide (13 to 15 Kg per extraction) and the resulting lower aqueous phases are removed from the 50 liter flask. To the product solution in the 50 liter flask is added tetrahydrofuran (4 to 5 Kg) and the resulting solution is extracted with water (13 to 15 Kg). The lower aqueous phase is removed and the product solution is concentrated under vacuum at 40° C. to 45° C. to provide the title compound as a viscous orange/brown oil (5.8 to 6.9 Kg).

EXAMPLE 11

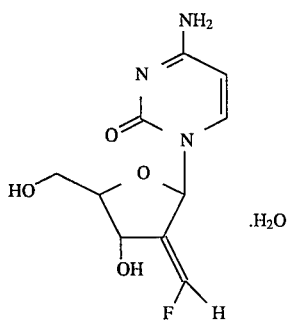

Preparation of (E)-2'-deoxy-2'(fluoromethylene)cytidine monohydrate.

The (2'Z)-2'-deoxy-2'-[fluoro(tributylstannyl)methylene]-3', 5'-O-[1,1,3,3-tetrakis(1-methylethyl)-1,3-disiloxanediyl]-cytidine (6.39 Kg) prepared in example 10 is dissolved in methanol (9.24 Kg). 50% wt potassium fluoride dihydrate (4.03 Kg diluted with 1.22 Kg of water) is added with stirring. The reaction is heated to 45° C. for 48 hours. The reaction is then concentrated under vacuum at a bath temperature of 30° C. The concentrate is partitioned between water (4.0 Kg) and ethyl acetate (4.0 Kg). The lower aqueous layer is collected and saved. The upper organic layer containing tributyltin compounds and tetraisopropyl-siloxyl compounds is discarded. The middle emulsion layer is filtered and the filtercake is rinsed with water (1.0 Kg) and ethyl acetate (1.0 Kg). The filtrate is allowed to separate and the lower aqueous layer is collected. The aqueous layers are then combined and rinsed with ethyl acetate (2 Kg). Diatomaceous earth (0.05 Kg) is added to the combined aqueous layers which is then vacuum filtered. The filtrate is concentrated under vacuum at a bath temperature of 30° C. Methanol (3.0 Kg) is added to the concentrate and the mixture is again concentrated under vacuum. The residue is then dissolved in methanol (5.0 Kg) and silica gel 60 (4.0 Kg, 100–200 mesh) is added. The mixture is evaporated with a continuous addition of isopropanol to maintain the original volume nearly constant. After approximately 20 Kg of distillate is collected, the slurry is added to a column containing silica gel (2.0 Kg) that has been preconditioned with isopropanol. The column is eluted with isopropanol until no product is detected in the fractions. The fractions are combined and concentrated to approximately 4 liters total volume. The slurry is filtered and the filtercake rinsed with isopropanol (1.0 Kg). The filtercake is air dried to a constant weight (0.83 Kg) to provide the crude anhydrous form of the title compound. This material is combined with similar batches and the total amount (3.82 Kg) is dissolved in water (22 Kg) and polish filtered. The filtrate is concentrated to 8–10 liters total volume under vacuum at a bath temperature of 30° C. The resulting slurry is cooled at 5° C. for 2 hours. The product is collected by vacuum filtration and rinsed with cold water (1.8 Kg). The filtercake is air dried to a constant weight (3.31 Kg, 99.8% pure by HPLC, corrected for water) to provide the title compound.

EXAMPLE 12

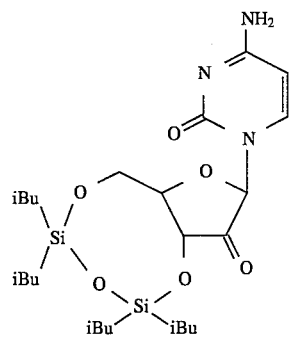

Preparation of 2'-Deoxy-2'-oxo-3',5'-O-[1,1,3,3-tetrakis(2-methyl-1-propyl)-1,3-disiloxanediyl]-cytidine.

The title compound can be prepared from cytidine (28.8 mol) and 1,3-dichloro-1,1,3,3-tetraisobutyldisiloxane (31.7 mol) in a manner analogous to the procedure described in example 8.

EXAMPLE 13

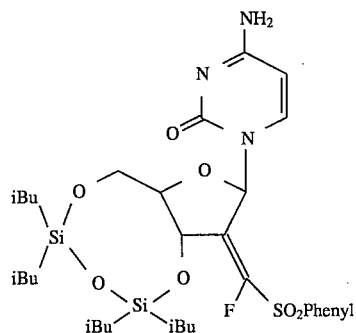

Preparation of (Z)-2'-[fluoro(phenylsulfonyl)methylene]-3', 5'-O-[1,1,3,3-tetrakis(2-methyl-1-propyl)-1,3-disiloxanediyl]-cytidine.

The title compound can be prepared from diethyl-1-fluoro-1-phenylsulfonylmethanephosphonate (4.483 mol) and ground 2'-Deoxy-2'-oxo-3',5'-O-[1,1,3,3-tetrakis(2-methyl-1-propyl)-1,3-disiloxanediyl]-cytidine (4.266 mol) prepared in example 12, in a manner analogous to the procedure described in example 9.

EXAMPLE 14

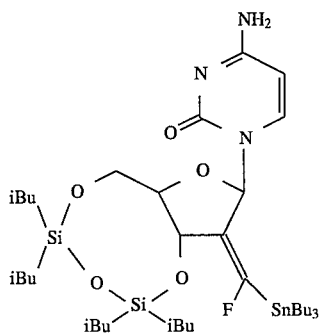

Preparation of (Z)-2'-deoxy-2'-[fluoro(tributylstannyl)methylene]-3',5'-O-[1,1,3,3-tetrakis(2-methyl-1-propyl)-1,3-disiloxanediyl]-cytidine.

The title compound can be prepared from (Z)-2'-[fluoro(phenylsulfonyl)methylene]-3',5'-O-[1,1,3,3'-tetrakis(2-methyl-1-propyl)-1,3-disiloxanediyl]-cytidine (1.327 Kg) prepared in example 13, tributyl tin hydride (2.5 to 2.7 equivalents) and azoisobutyronitrile (44 to 55 g, AIBN) in a manner analogous to the procedure described in example 10.

EXAMPLE 15

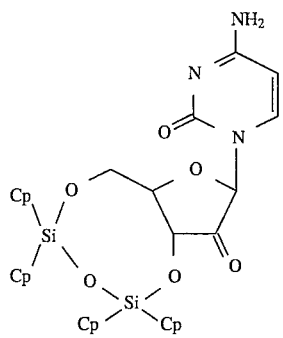

Cp represents a cyclopentyl substituent

Preparation of 2'-Deoxy-2'-oxo-3',5'-O-[1,1,3,3-tetrakis(cyclopentyl)-1,3-disiloxanediyl]-cytidine.

The title compound can be prepared from cytidine (28.8 mol) and 1,3-dichloro-1,1,3,3-tetracyclopentyldisiloxane (31.7 mol) in a manner analogous to the procedure described in example 8.

EXAMPLE 16

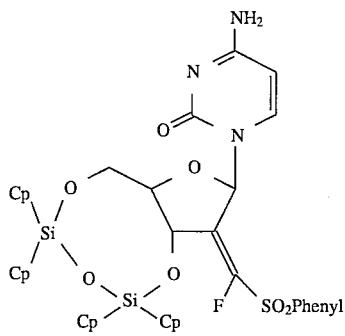

Preparation of (Z)-2'-[fluoro(phenylsulfonyl)methylene]-3',5'-O-[1,1,3,3-tetrakis(cyclopentyl)-1,3-disiloxanediyl]cytidine.

The title compound can be prepared from diethyl-1-fluoro-1-phenylsulfonylmethanephosphonate (4.483 mol) and ground 2'-Deoxy-2'-oxo-3',5'-O-[1,1,3,3-tetrakis(cyclopentyl)-1,3-disiloxanediyl]-cytidine (4.266 mol) prepared in example 15, in a manner analogous to the procedure described in example 9.

EXAMPLE 17

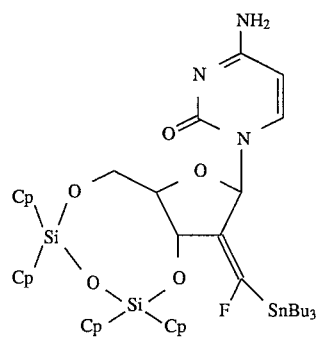

Preparation of (Z)-2'-deoxy-2'-[fluoro(tributylstannyl)methylene]-3',5'-O-[1,1,3,3-tetrakis(cyclopentyl)-1,3-disiloxanediyl]-cytidine.

The title compound can be prepared from (Z)-2'-[fluoro(phenylsulfonyl)methylene]-3',5'-O-[1,1,3,3-tetrakis(cyclopentyl)-1,3-disiloxanediyl]-cytidine (1.327 Kg) prepared in example 16, tributyl tin hydride (2.5 to 2.7 equivalents) and azoisobutyronitrile (44 to 55 g, AIBN) in a manner analogous to the procedure described in example 10.

Following the respective procedures, the anhydrous final product prepared in example 7, (E)-2'-deoxy-2'(fluoromethylene)cytidine and the monohydrate of the final product prepared in example 11, (E)-2'-deoxy-2'(fluoromethylene)cytidine monohydrate can each be prepared in an analogous manner from either (Z)-2'-deoxy-2'-[fluoro(tributylstannyl)methylene]-3',5'-O-[1,1,3,3-tetrakis(2-methyl-1-propyl)-1,3-disiloxanediyl]-cytidine prepared in example 14 or (Z)-2'-deoxy-2'-[fluoro(tributylstannyl)methylene]-3',5'-O-[1,1,3,3-tetrakis(cyclopentyl)-1,3-disiloxanediyl]-cytidine prepared in example 17.

The present invention provides a method of treating a patient afflicted with a neoplastic disease state comprising the administration thereto of an effective antineoplastic amount of ionizing or nonionizing radiation, or an effective antineoplastic amount of a DNA-reactive chemotherapeutic agent, in conjunctive therapy with an effective sensitizing amount of a compound of the formula (I). The term "neoplastic disease state" as used herein refers to an abnormal state or condition characterized by rapidly proliferating cell growth or neoplasm. Neoplastic disease states for which treatment with a compound of formula (I) will be particularly useful include: Leukemias such as, but not limited to, acute lymphoblastic, chronic lymphocytic, acute myeloblastic and chronic myelocytic; Carcinomas and adenocarcinomas, such as, but not limited to, those of the cervix, oesophagus, stomach, small intestines, colon, lungs (both small cell and large cell), breast and prostate; Sarcomas, such as, but not limited to, oesteroma, osteosarcoma, lipoma, liposarcoma, hemangioma and hemangiosarcoma; Melanomas, including amelanotic and melanotic; and mixed types of neoplasias such as, but not limited to carcinosarcoma, lymphoid tissue type, follicullar reticulum, cell sarcoma and Hodgkins Disease. Neoplastic disease states for which treatment with a compound of formula (I) will be particularly preferred include carcinomas and adenocarcinomas, particularly of the breast, prostate and lung.

As used herein, the term "patient" refers to a mammal, including mice, rats, dogs and humans, which is afflicted with a neoplastic disease state or cancer such that it is in need of cancer radiation therapy or chemotherapy with a DNA-reactive chemotherapeutic agent.

Ionizing radiation is high energy radiation, such as an X-ray or a gamma ray, which interacts to produce ion pairs in matter. Exposure to ionizing radiation may occur as the result of environmental radiation, such as resulting from a nuclear explosion, a spill of radioactive material, close proximity to radioactive material and the like. More commonly, exposure to ionizing radiation may occur as the result of radiological medical procedures such as radiation therapy for various types of cancers. Nonionizing radiation of ultraviolet wavelengths has just enough energy to cause photochemical reactions but is not sufficiently energetic to cause ionization. The principle source of ultraviolet radiation is the sun. Ultraviolet radiation is capable of penetrating only the uppermost layers of the skin where its deposition causes skin cancer. Ultraviolet light is used clinically in photo-dynamic therapy of skin diseases such as psoriasis and in skin cancers. These applications rely on previous exposure to an ultraviolet sensitizing moiety.

DNA-reactive agents are those agents, such as alkylating agents, cross-linking agents, and DNA intercalating agents, which interact covalently or non-covalently with cellular DNA causing certain deleterious cellular effects. For example, DNA-reactive agents include cisplatin, cyclophosphamide, diethylnitrosoamine, benzo(a)pyrene, carboplatin, doxorubicin, mitomycin-C and the like. Many of these DNA-reactive agents, such as cisplatin, cyclophosphamide, doxorubicin and mitomycin-C are useful in cancer therapy as DNA-reactive chemotherapeutic agents.

Deleterious cellular effects caused by exposure to ionizing radiation or to a DNA-reactive agent include damage to cellular DNA, such as DNA strand break, disruption in cellular function, such as by disrupting DNA function, cell death, and the like.

A therapeutically effective antineoplastic amount of ionizing or nonionizing radiation, a DNA-reactive agent, or a compound of formula (I), refers to an amount which is effective, upon single or multiple dose administration to the patient, in controlling the growth of the neoplasm or in prolonging the survivability of the patient beyond that expected in the absence of such treatment. As used herein, "controlling the growth" of the neoplasm refers to slowing, interrupting, arresting or stopping its growth and metastases and does not necessarily indicate a total elimination of the neoplasm.

A therapeutically effective amount can be readily determined by the attending diagnostician, as one skilled in the art, by the use of known techniques and by observing results obtained under analogous circumstances. In determining the therapeutically effective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

An effective antineoplastic amount of ionizing or nonionizing radiation can be readily determined by one of ordinary skill in the art. An effective antineoplastic amount of a DNA-reactive agent or a compound of formula (I) is expected to vary from about 0.1 milligram per kilogram of body weight per day (mg/kg/day) to about 100 mg/kg/day. Preferred amounts are expected to vary from about 0.5 to about 10 mg/kg/day.

According to the present invention, administration to a patient of a compound of formula (I) prior to or during radiation therapy or chemotherapy with a DNA-reactive chemotherapeutic agent will provide a sensitization of the cancer cells of the patient. The deleterious cellular effects on cancer cells caused by the treatment of the patient with ionizing or nonionizing radiation or with a DNA-reactive agent are thus enhanced.

An effective sensitizing amount of a compound of formula (I) refers to that amount which is effective, upon single or multiple dose administration to a patient, in enhancing the severity or in extent the deleterious cellular effects to cancer cells caused by exposure to or treatment with ionizing or nonionizing radiation or a DNA-reactive agent. An effective sensitizing amount of a compound of formula (I) also refers to that amount which is effective, upon single or multiple dose administration to a cell, in enhancing the severity or in extent the deleterious cellular effects to cancer cells caused by exposure to or treatment with ionizing or nonionizing radiation or a DNA-reactive agent.

An effective sensitizing amount for administration to a patient can be readily determined by the attending diagnostician, as one skilled in the art, by the use of known techniques and by observing results obtained under analogous circumstances. In determining the effective sensitizing amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

The compounds of formula (I) may be administered as single doses or as multiple doses and are ordinarily administered prior to and/or during exposure to ionizing or nonionizing radiation or to DNA-reactive agents. Generally, where a compound of the present invention is administered in conjunction with radiation therapy, the compound of the present invention will be administered in single or multiple doses prior to radiation therapy following a schedule calculated to provide the maximum selective sensitizing effect during radiation therapy. Generally, where a compound of the present invention is administered in conjunction with a DNA-reactive chemotherapeutic agent, the compound of the present invention will be administered in single or multiple doses prior to and during chemotherapy following a schedule calculated to provide the maximum selective sensitizing effect during chemotherapy.

The details of the dosing schedule for the compounds of the present invention necessary to provide the maximum selective sensitizing effect upon exposure to ionizing radiation or to a DNA-reactive agent can be readily determined by an attending physician, as one skilled in the art, by the use of known techniques and by observing results obtained under analogous circumstances.

An effective sensitizing amount of a compound of formula (I) for administration to a patient will vary from about 0.01 milligram per kilogram of body weight per day (mg/kg/day) to about 100 mg/kg/day. Preferred amounts are expected to vary from about 0.05 to about 10 mg/kg/day.

The compounds of formula (I) can be administered to a patient in any form or mode which makes the compound bioavailable in effective amounts, including oral and parenteral routes. For example, compounds of formula (I) can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

Pharmaceutical compositions comprising a therapeutically effective amount of a compound of formula (I), are disclosed in European Patent Application Publication No. 0 372 268, published Jun. 13, 1990.

The present invention also provides a method of treating a patient afflicted with a neoplastic disease state comprising the administration thereto of an effective antineoplastic amount of ionizing or nonionizing radiation or an effective antineoplastic amount of a DNA-reactive chemotherapeutic agent in conjunctive therapy with an effective antineoplastic amount of a compound of formula (1), wherein a synergistic effect results.

As used herein, the term "synergistic effect" is achieved when a greater antineoplastic effect results with a conjunctive therapy than use of either drug or therapy alone. One advantage of conjunctive therapy with a synergistic effect is that lower dosages of one or both of the drugs or therapies may be used so that the therapeutic index is increased and toxic side effects are reduced.

Furthermore, the present invention provides for a method of treating a patient in need of radiation therapy, or in need of chemotherapy with a DNA-reactive chemotherapeutic agent, comprising administering to said patient a sensitizing amount of a compound of formula (1).

The present invention further provides for a method of sensitizing cancer cells of a patient to the deleterious effects caused by exposure to ionizing or nonionizing radiation, or by exposure to a DNA-reactive agent, comprising contacting said cells with a sensitizing amount of a compound of formula (1).

An effective sensitizing amount of a compound of formula (I) for contacting a cell will vary from about 100 micromolar to about 5 millimolar in concentration.

As with any group of structurally related compounds which possesses a particular generic utility, certain groups and configurations are preferred for compounds of formula (I) in their end-use application. The preferred compounds according to the present invention are (Z)-2'-deoxy-2'-fluoromethylidenecytidine and (E)-2'-deoxy-2'-fluoromethylidenecytidine, or racemic mixtures thereof, i.e. 2'-deoxy-2'-fluoromethylidenecytidine, with (E)-2'-deoxy-2'-fluoromethylidenecytidine being the most preferred compound.

The following studies are provided in order to support the methods of use of the present invention. These studies are intended to be illustrative only and are not to be construed to limit the scope of the invention in any way.

EXAMPLE 18

Radiosensitizing Effect of
2'-deoxy-2'-fluoromethylidenecytidine on HeLa cells

Cell Culture

HeLa S-3 cells were grown and maintained in modified Eagles's medium containing 10% fetal bovine serum in a humidity and $CO_2$-controlled incubator. Experimental studies were initiated on exponential cultures growing in 60 mm tissue culture dishes at treatment densities of $3-7\times10^5$ cells/dish. The doubling time of HeLa S-3 cultures was determined to be approximately 18 hours.

Drug Treatment

2'-deoxy-2'-fluromethylidenecytidine was synthesized as described by McCarthy, J. R., et al.; *J Am. Chem. Soc.* 113: 7439–7440 (1991). Drug was dissolved in distilled water just prior to use and was diluted 1:100 through addition of the proper volume to cultured cells. For ultraviolet irradiation studies, drug was added only during the repair period following irradiation. For X-irradiation studies, drug was added to cultures 1 hour prior to irradiation and remained on cells during irradiation. Fresh media with no drug was added to cultures for repair incubations.

Irradiation of Cultures

For ultraviolet irradiation, all media was removed from cultures and, with the lid removed, dishes were exposed to 1.4 $J/M^2$ of $UV_{254}$ light emitted from a G.E. germicidal lamp. Fresh media with or without drug was then added to cultures during the subsequent repair period. In some cases, cells were harvested immediately in order to establish a $T_{zero}$ value for DNA strand breaks. X-irradiation of cultures was carried out in a TFI Bigshot X-ray unit at 3 mA, 50 keV, filtered with 1.5 mm Be and delivering 0.56 Gy/min to the cells (through the lid and 5 mls of media) as determined by a Victoreen ionization chamber calibrated in the 10 to 50 keV range. Following X-irradiation, cultures were either returned to the incubator for repair studies, or were harvested immediately for colony forming ability assays. $D_0$ values were calculated from survival curves computer plotted by linear regression analysis (Excel 5.0, Microsoft).

Colony Forming Ability Assays

The ability of cells to form colonies after irradiation was determined by standard methods. Cultures treated 1 h with 2'-deoxy-2'-fluromethylidenecytidine were irradiated and immediately typsinized, counted and replated in 5 mls media containing the appropriate number of cells (500 for untreated cultures and cultures exposed to 2.8 Gy X-rays; 2,000 for cultures exposed to 20 $J/M^2$ UV; 5,000 for cultures exposed to 5.6 Gy X-rays and 10,000 for cultures exposed to 8.4 Gy X-rays). Cultures were grown for 10 days at which time colonies of 1.0–2.0 mm (50–200 cells) were evaluated by methanol fixation and Dif-Qwik staining. Untreated HeLa cells exhibited cloning efficiencies in the range of 34 to 46% using this protocol.

Nucleoid Sedimentation Analysis of DNA Strand Break Repair

To demonstrate the formation and repair of DNA strand breaks in irradiated cultures, cells were subjected to nucleoid sedimentation through neutral sucrose gradients. This assay measures the amount of unwinding of cellular DNA which has been depleted of most protein and RNA (the resultant chromosome body being termed a nucleoid). Sites of DNA strand interruptions serve as unwinding points. As the DNA becomes increasingly unwound, its migration through the gradient is impeded relative to that from untreated control cells. The linearity of this assay has been previously calibrated with X-ray doses in Snyder, R. D.; *Mutat. Res.* 193: 237–246 (1988). The assay was conducted as follows: cells were harvested in cold EDTA-saline and $2.5\times10^5$ cells were immediately added to a 300 µl lysis layer (comprised of 1.9 M NaCl, 100 mM EDTA, 32 mM Tris-HCl pH 8.0, and 0.5 percent Triton-X100) on top of a 15–30 percent linear neutral sucrose gradient. Gradients also contained Hoechst dye 33258 for DNA visualization. Following a 20 min lysis period, gradients were spun for 45 min at 14,000–17,000 rpm in an SW 50.1 rotor at 18° C. The distance sedimented by nucleoids was determined by DNA/dye fluorescence under ultraviolet light. Variability was usually no greater than 10 percent.

Results

HeLa cells treated for 1 hour with 5 or 10 μM FMdC displayed a small, but reproducible reduction in colony forming ability; 94.2±3 and 89.6±7 percent control, respectively. However, no increase in trypan blue uptake was observed immediately following treatment indicating that these short treatments were not overtly toxic. Longer treatment times at much lower doses (10–100 nM) were found to be cytostatic, and/or cytotoxic and in some instances to induce cellular changes reminiscent of programmed cell death.

Treatment of HeLa cells for 1 hour prior to exposure to a graded series of X-irradiation doses altered their radiosensitivity (FIG. 1). Non-drug treated cultures exhibited a $D_0$ of 2.28 while those treated 5 or 10 μM FMdC had $D_0$ values of 1.65 and 1.35, respectively indicating substantially increased radiosensitivity. It has previously been demonstrated that the survival curve of X-irradiated HeLa cells does not feature a prominent repair shoulder; Snyder, R. D., et al., *Radiation Res.* 137: 67–75 (1994). For this reason, no attempt was made to determine radiosensitivities in the very low dose range required for this type of analysis. Instead, in order to determine if increased radiosensitivity is accompanied by any deficit in DNA repair, DNA strand break formation and resealing was examined directly by nucleoid sedimentation.

HeLa cells were incubated with 10 μM FMdC for 1 hour and then X-irradiated. Drug-containing media was replaced with fresh media without drug for analysis of repair. The nucleoid sedimentation procedure provides a very sensitive measure of the sealing of DNA strand breaks. Early resealing (0–60 min) is generally considered to represent single strand break (SSB) repair while that occurring after 60 minutes is primarily double strand break (DSB) repair and reestablishment of normal chromatin supercoiling. See generally, Snyder, R. D.; *Int. J. Rad. Biol.* 55: 773–782 (1989); Mattern, M. R., et al.; *Biochem. Biophys. Res. Commun.*, 112: 1077–1084; and Dikomey, E., Franzke, J.; *Int. J. Rad. Biol.* 50: 893–908 (1986). FIG. 2 demonstrates that X-irradiated (2.8 Gy) HeLa cells repair most of their DNA SSB within the first 30–60 minutes after irradiation despite the fact that at this X-ray dose, only approximately 16.8% of the cells are capable of forming colonies. In fact, the same repair kinetics are exhibited by HeLa cells having received an X-ray dose resulting in less than 1% colony forming ability (see Snyder, R. D.; *Int. J. Rad. Biol.* 55:773–782 (1989)). This suggests that DNA SSB repair is not sensitive to the cycling status of cells and is not dose dependent as has been suggested to be the case for DNA DSB repair, Iliakis, G., et al.; *Int. J. Radiat. Biol.*, 59:927–939 (1991). In contrast, cells treated with 10 μM FMdC one hour before irradiation exhibit marked retardation in the rate of strand resealing which is not complete even after 2 hours of incubation. At this 2 hour timepoint, 25% of FMdC treated irradiated cells show trypan blue uptake indicating loss of viability. Sealing of strand breaks was not further compromised if FMdC was also present during the repair period even though this additional 2 hour exposure to drug resulted in markedly greater toxicity (65% Trypan blue uptake). This suggests that sufficient drug had accumulated in cells during the 1 H exposure period to maximally interfere with the DNA repair process.

FMdC treatment also sensitized HeLa cells to UV irradiation. FIG. 3 demonstrates that a 1 h exposure to 10 μM FMdC impaired the ability of cells to form colonies following 20 or 40 $J/M^2$ UV irradiation, relative to cells not treated with FMdC.

Ultraviolet irradiation does not induce DNA strand breaks directly. Rather, transient breaks arise as a result of the DNA excision repair process acting at sites of pyrimidine dimers and (6-4) photoproducts. Repair at these sites, once initiated, is usually complete within a few minutes and cannot be visualized in the absence of inhibitors of repair. Thus, FIG. 4 demonstrates that UV-irradiation alone does not give rise to an appreciable decrease in sedimentation of nucleoids when measured 1 hour post-irradiation. However, if repair is allowed to proceed in the presence of the repair inhibitory deoxycytidine analog, ara-C, nucleoids sediment more slowly indicating the existence of stable single strand breaks. FIG. 4 also shows that FMdC present during repair has the same effect as ara-C and that neither ara-C nor FMdC induce significant DNA strand breakage in the absence of irradiation. These studies, in contrast to the X-ray repair studies, were conducted without FMdC pretreatment of cells. This protocol was established in order to conform to most UV inhibitor studies (see Collins, A., Downes, C. S.; Johnson, R. T., eds. *DNA Repair and Its Inhibition.* Oxford: IRL Press; 1984) predicated on the protracted kinetics of UV repair relative to X-ray repair; Snyder, R. D., et al.; *Biophys. Journal*, 35:339–350 (1981).

Figure 1:
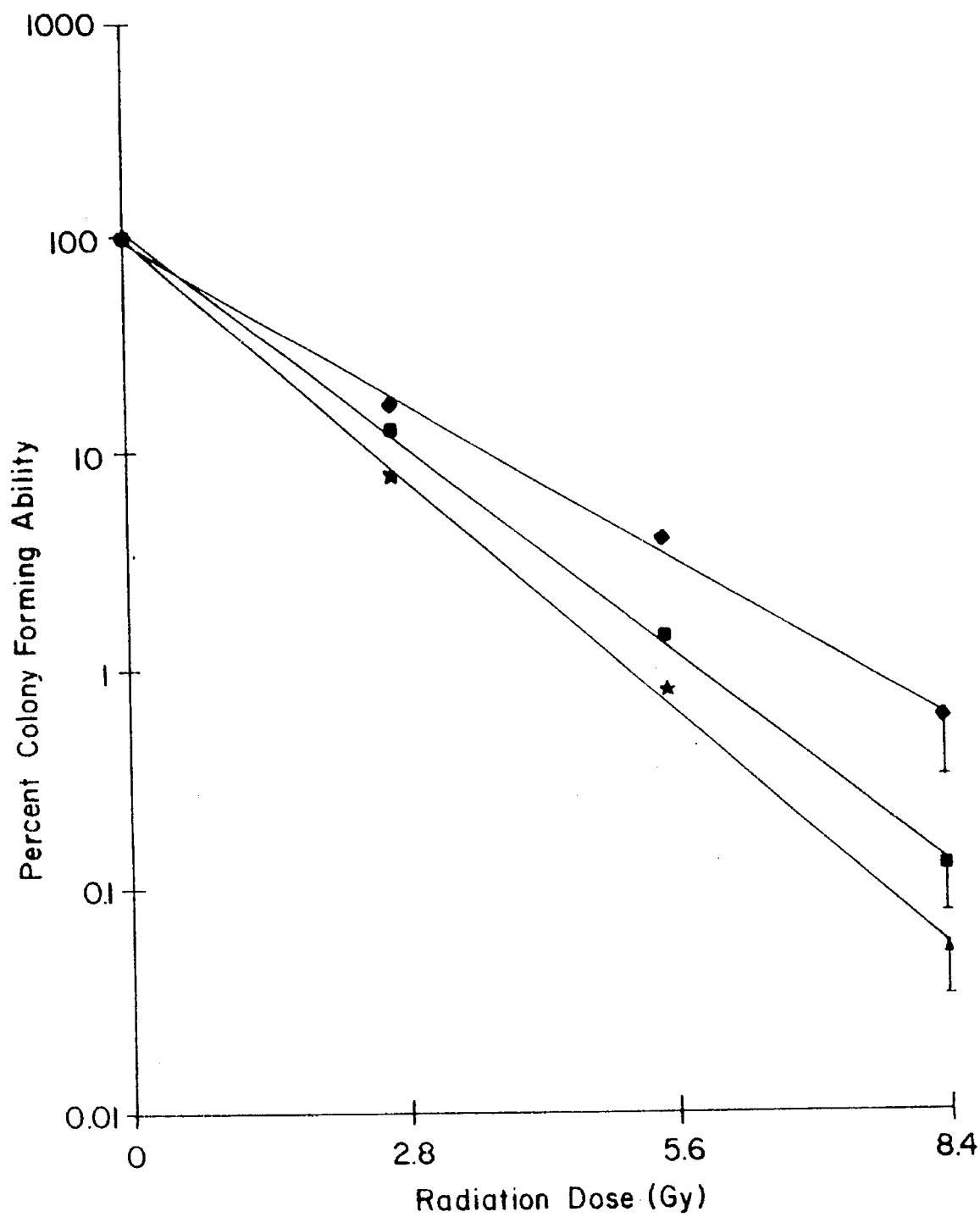
FIG. 1 shows the effect of FMdC on the radiation dose-response curve for HeLa cells. HeLa cells were X-irradiated after a 1 hour incubation in media alone (♦), or in media containing 5 μM FMdC (■), or 10 μM FMdC (▲). Cells were immediately harvested, counted and replated at clonal density as described in Example 18. Error bars represent standard error of the mean in 6 experiments.
Figure 2:
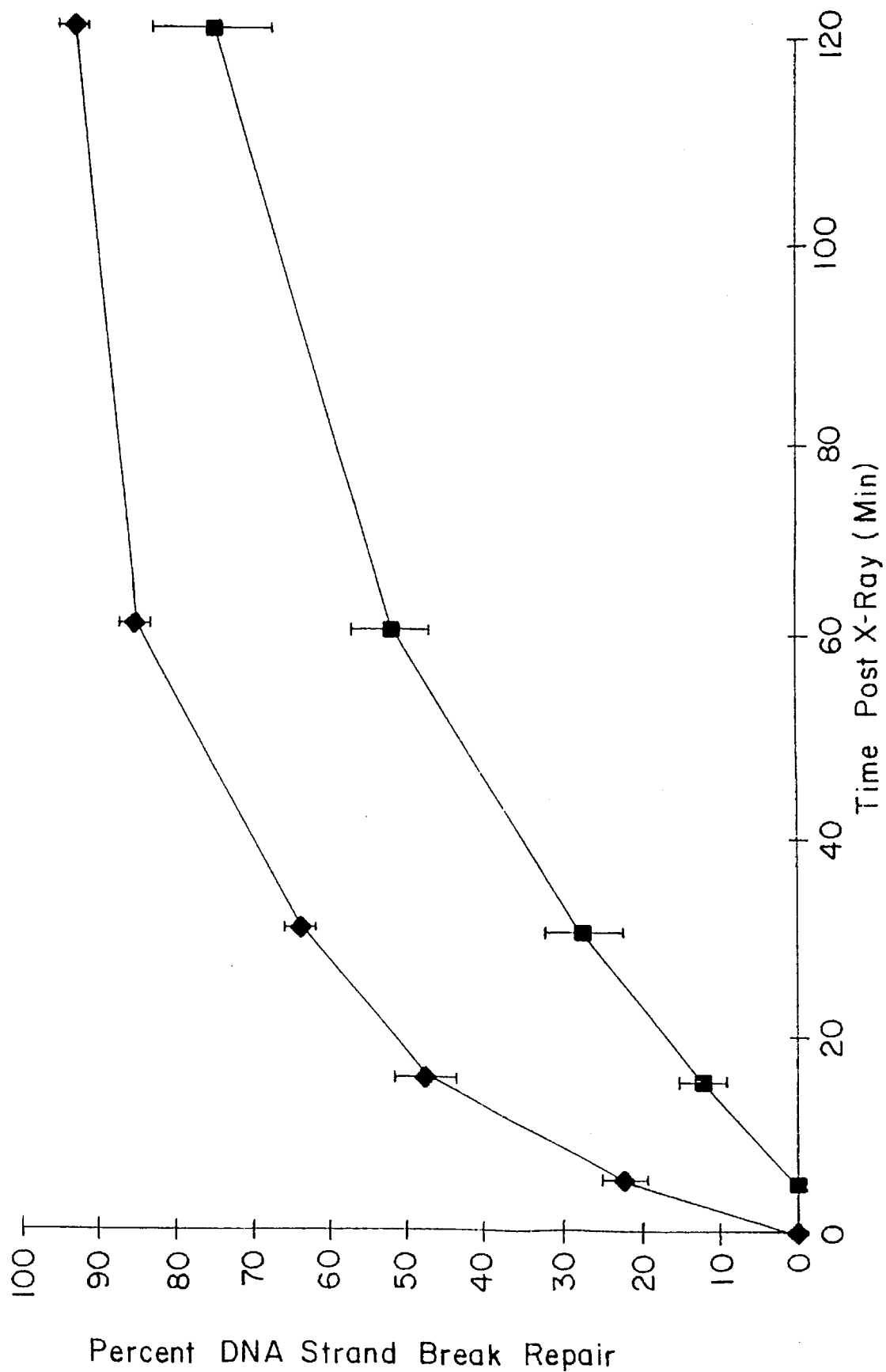
FIG. 2 shows the effect of FMdC on X-ray induced DNA single strand break repair. HeLa cells were exposed to 10 μM FMdC (■) for 1 hour or were left untreated (●). Cultures were irradiated with 2.8 Gy X-irradiation, drug-containing media was replaced with fresh media containing no drug, and dishes were either harvested immediately or after various repair incubation times. Cells were subjected to neutral sucrose sedimentation as described in Example 18. Percent DNA strand break repair was calculated as the fractional return of nucleoids from the X-irradiated position to the unirradiated control position in the gradient. Error bars represent the standard error of the mean in 3 experiments.
Figure 3:
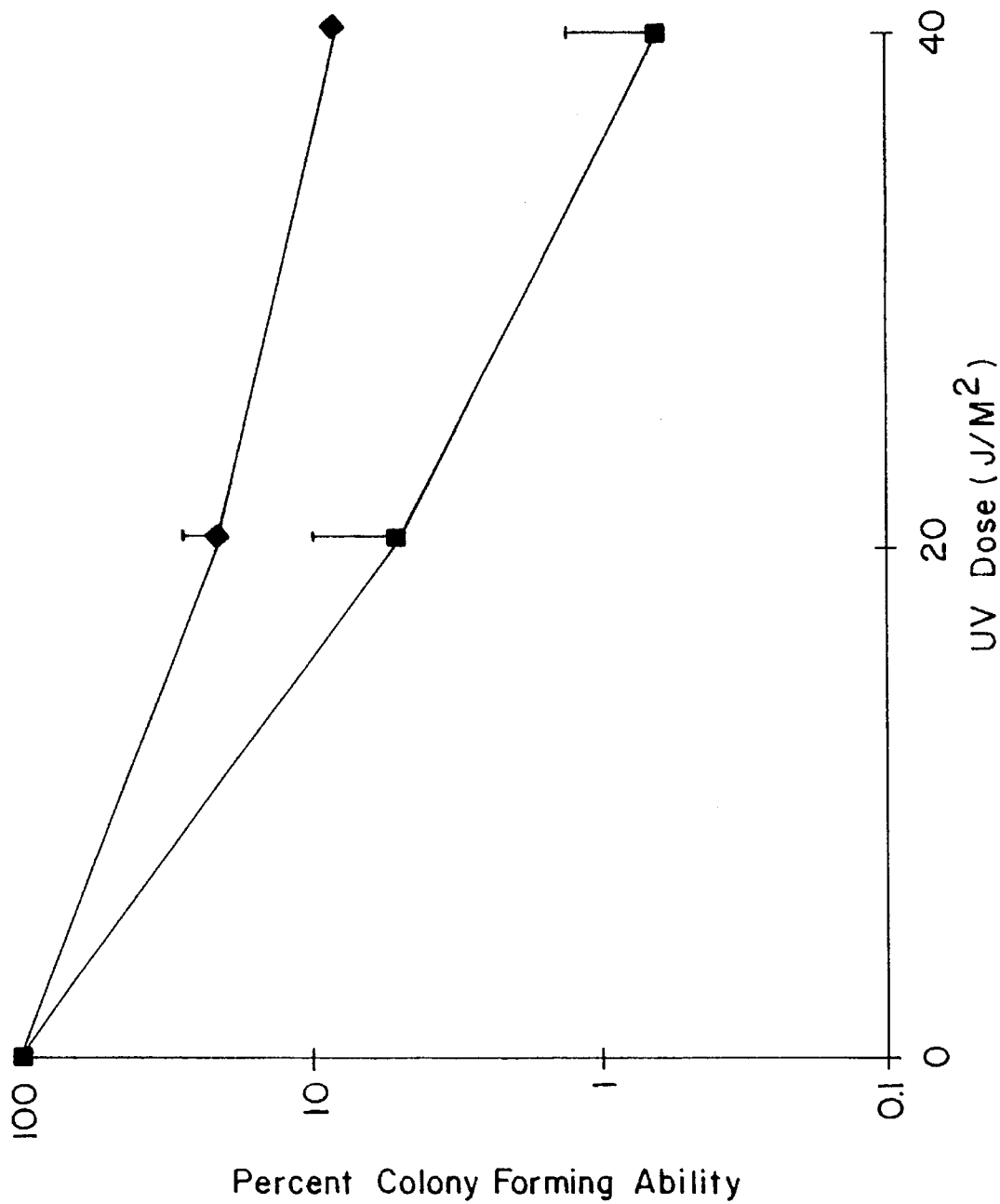
FIG. 3 shows the effect of FMdC on survival of HeLa cells following ultraviolet irradiation. Cells exposed to 10 μM FMdC (■) or were left untreated (●) for 1 h prior to UV-irradiation. Cells were irradiated, immediately harvested and replated at clonal density as described in Example 18. Error bars represent standard error of the mean in 3 experiments.
Figure 4:
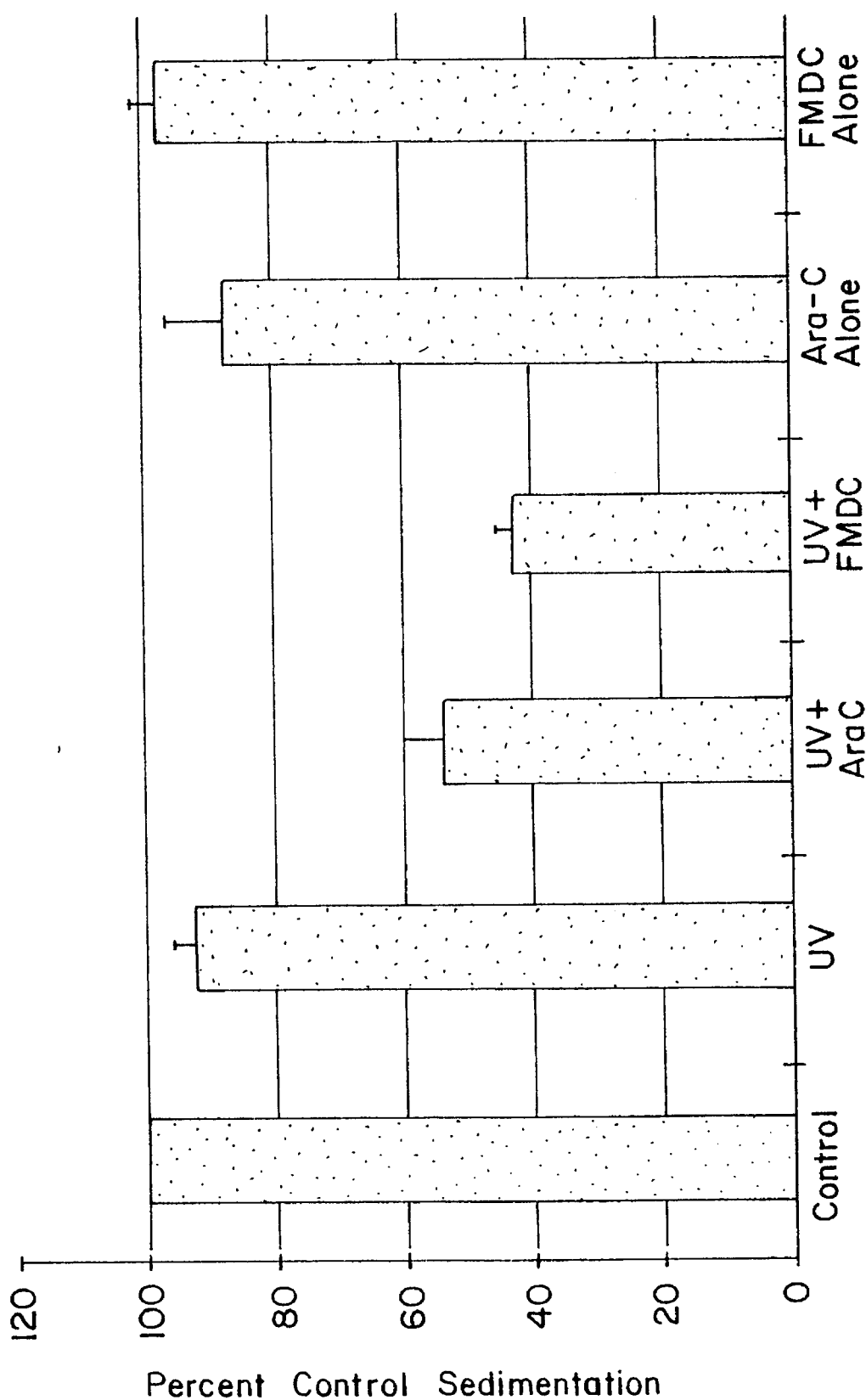
FIG. 4 shows the effect of FMdC and ara-C on UV excision repair in HeLa cells. Cells were UV-irradiated (1.4 $J/M^2$) and incubated in fresh media with no drug, 1 μM ara-C, or 1 μM FMdC. After 1 hour, cells were harvested and analyzed by neutral sucrose sedimentation. Error bars represent the standard error of the mean in 4 separate experiments.

What is claimed is:

1. A method of treating a patient afflicted with a neoplastic disease state comprising the administration thereto of an effective antineoplastic amount of ionizing or nonionizing radiation in conjunctive therapy with an effective sensitizing amount of a compound of the formula

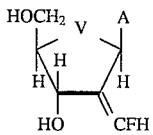   (I)

wherein

V is oxy or methylene and

A is a radical of the formula

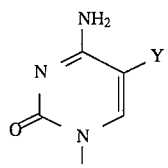

wherein Y is hydrogen, $C_1$–$C_4$ alkyl or $C_1$–$C_4$ alkoxy; or a pharmaceutically acceptable salt thereof.

2. A method according to claim 1 wherein V is oxy.

3. A method according to claim 2 wherein Y is hydrogen.

4. A method according to claim 1 wherein the neoplastic disease state is a leukemia.

5. A method according to claim 1 wherein the neoplastic disease state is a carcinoma.

6. A method of treating a patient afflicted with a neoplastic disease state comprising the administration thereto of an effective antineoplastic amount of ionizing or nonionizing radiation in conjunctive therapy with an effective antineoplastic amount of a compound of claim 1, wherein a synergistic effect results.

7. A method of treating a patient in need of radiation therapy comprising administering to said patient a sensitizing amount of a compound of claim 1.

8. A method of sensitizing cancer cells of a patient to the deleterious effects caused by exposure to ionizing or nonionizing radiation comprising contacting said cells with a sensitizing amount of a compound of claim 1.

* * * * *

UNITED STATES PATENT AND TRADEMARK OFFICE
CERTIFICATE OF CORRECTION

PATENT NO.  : 5,595,979

DATED       : January 21, 1997

INVENTOR(s) : Ronald D. Snyder

It is certified that error appears in the above-identified patent and that said Letters Patent is hereby corrected as shown below:

"CFH OH" at Column 6, line 33, and should read --CFH --.

"(X) 2OP=CF(S02Ar)" at Column 13, line 10, and should read --$(X)_2OP=CF(SO_2Ar)$--.

"(CI/CH4)" at Column 17, line 7, and should read --$(CI/CH_4)$.

Signed and Sealed this

Twenty-sixth Day of May, 1998

Attest:

BRUCE LEHMAN

Attesting Officer

Commissioner of Patents and Trademarks